United States Patent
Hendry

(10) Patent No.: US 12,114,663 B2
(45) Date of Patent: Oct. 15, 2024

(54) COMPOSITIONS AND METHODS FOR INSECT CONTROL

(71) Applicant: Cornell University, Ithaca, NY (US)

(72) Inventor: Tory Hendry, Ithaca, NY (US)

(73) Assignee: Cornell University, Ithaca, NY (US)

( * ) Notice: Subject to any disclaimer, the term of this patent is extended or adjusted under 35 U.S.C. 154(b) by 964 days.

(21) Appl. No.: 16/968,459

(22) PCT Filed: Feb. 11, 2019

(86) PCT No.: PCT/US2019/017427
§ 371 (c)(1),
(2) Date: Aug. 7, 2020

(87) PCT Pub. No.: WO2019/157422
PCT Pub. Date: Aug. 15, 2019

(65) Prior Publication Data
US 2020/0397004 A1    Dec. 24, 2020

Related U.S. Application Data

(60) Provisional application No. 62/628,652, filed on Feb. 9, 2018.

(51) Int. Cl.
*A01N 63/27* (2020.01)
*A01G 9/14* (2006.01)
*A01G 31/00* (2018.01)

(52) U.S. Cl.
CPC ............... *A01N 63/27* (2020.01); *A01G 9/14* (2013.01); *A01G 31/00* (2013.01)

(58) Field of Classification Search
CPC .................... A01N 47/44; C12N 1/20
See application file for complete search history.

(56) References Cited

U.S. PATENT DOCUMENTS

| 4,766,077 A | 8/1988 | Orser et al. |
| 2012/0210637 A1 | 8/2012 | Kamahara |
| 2017/0081632 A1 | 3/2017 | Shih et al. |

FOREIGN PATENT DOCUMENTS

| CN | 107267424 A | 10/2017 |
| WO | 2013/024486 A1 | 2/2013 |
| WO | 2016/120478 A1 | 8/2016 |

OTHER PUBLICATIONS

Trapet et al. Plant Physiology, 171, 2016, 675-693.*
Over Stavrinides et al. Applied and Environmental Microbiology, 2009, 75/7, 2230-2235.*
By Loper et al. Molecular Plant-Microbe Interactions, 4, 1, 5-13, 1991.*
Ribiero et al., Pesq. agropec. bras., Brasilisa, 52, 10, 2017, 956-959.*
Kupferschmied, P., et al., Promise for plant pest control: root-associated pseudomonads with insecticidal activities, Frontiers in Plant Science, Jul. 31, 2013, vol. 4, pp. 1-17.
Weigert, M., Manipulating virulence factor availability can have complex consequences for infections, Evol. Appl., Oct. 24, 2016, vol. 10, No. 1, pp. 91-100.
Saxon, E., Drawing the line, BMC Biology, Oct. 2, 2015, vol. 13, 1 page.
Ribeiro, C.M.C., et al., Pyoverdine use for the control of passion fruit bacterial blight, Pesquisa Agropecuária Brasileira, Oct. 2017, vol. 52, No. 10, pp. 956-959.
Sharifi, R., et al., Pyoverdine production in Pseudomonas fluorescens UTPF5 and its association with suppression of common bean damping off caused by Rhizoctonia solani (Kühn), Journal of Plant Protection Research, 2010, vol. 50, No. 1, pp. 72-78.
Hendry, T.A., et al., A highly infective plant-associated bacterium influences reproductive rates in pea aphids, Royal Society Open Science, Feb. 1, 2016, vol. 3, 10 pages.
Lindow, S.E., Competitive Exclusion of Epiphytic Bacteria by Ice-Pseudomonas syringae Mutants, Applied Environmental Microbiology, Oct. 1987, vol. 53, pp. 2520-2527.
Byrne, J.M., et al., Biological control of bacterial spot of tomato under field conditions at several locations in North America, Biological Control, Jan. 13, 2005, vol. 32, pp. 408-418.
Burr, T.J., Effectiveness of Bacteria and Yeasts from Apple Orchards as Biological Control Agents of Apple Scab, Biological Contro, 1996, vol. 6, pp. 151-157.

* cited by examiner

*Primary Examiner* — Kyle A Purdy
(74) *Attorney, Agent, or Firm* — Hodgson Russ LLP

(57) ABSTRACT

Provided are compositions and methods for use in deterring insects, such as aphids, from damaging plants. A method is provided and involves applying to one or more plants: i) bacteria that produce pyoverdine that emits fluorescent light that is detected by the insects and causes the insects to avoid the plant(s), wherein the bacteria are applied such that that there are more than $10^5$ bacterial cells per 3 cm$^2$ of plant surface, ii) a composition that contains at least 0.00005 mg of isolated pyoverdine that emits fluorescent light that is detected by the insects and causes the insects to avoid the plant(s), and combinations thereof. Also provided is a system for use in plant pest control in a confined space, including in structures such as greenhouses and hydroponic growing containers. The system includes one or more light sources that only emit light having a wavelength of 450-525 nm.

2 Claims, 13 Drawing Sheets

COMPOSITIONS AND METHODS FOR INSECT CONTROL

CROSS-REFERENCE TO RELATED APPLICATIONS

This application claims priority to U.S. provisional patent application No. 62/628,652, filed Feb. 9, 2018, the disclosure of which is incorporated herein by reference.

STATEMENT REGARDING FEDERALLY SPONSORED RESEARCH

This invention was made with government support under grant no. 2017-67013-26516, awarded by the United States Department of Agriculture. The government has certain rights in the invention.

FIELD

The disclosure relates to compositions and methods for reducing the impact of pest insects on plants, and in particular insects of the order Hemiptera, and more particularly insects of the suborder Sternorrhyncha, including but not necessarily limited to aphids.

BACKGROUND

Aphids are persistent pests that impact a wide variety of plants, including agricultural crops, ornamental plants, and a wide variety of other plant types. There is an ongoing and unmet need for improved approaches to reducing the presence of such pests on plants. The present disclosure is pertinent to this need.

SUMMARY

The present disclosure provides compositions and methods that are useful for deterring aphids from damaging plants. Damage to plants is deterred by causing aphids to avoid the plants due to the presence of bacteria that produce pyoverdine, and/or to the presence pyoverdine itself. In one approach the disclosure thus provides a method for causing insects such as aphids to avoid contacting one or more plants. The method comprises applying to one or more plants:
  i) bacteria that produce pyoverdine that emits fluorescent light that is detected by the insects and causes the insects to avoid the plant(s), wherein the bacteria are applied such that that there are more than $10^5$ bacterial cells per 3 $cm^2$ of plant surface,
  ii) a composition comprising isolated pyoverdine that emits fluorescent light that is detected by the insects and causes the insects to avoid the plant(s); the composition is applied such that at least 0.00005 mg of the pyoverdine in a 3 $cm^2$ plant surface area is present; or
  iii) a combination of i) and ii).

In embodiments, subsequent to applying i), ii) or iii) the plants are insect free, or are in contact with fewer insects than a control, such as a control that has a lower density of bacteria, or less pyoverdine.

In certain approaches, the plants that are exposed to the bacteria/compositions described herein are in a population of plants. The disclosure includes applying the bacteria and/or isolated pyoverdine-containing compositions to all of the plants in the population, and also includes applying the bacteria and/or isolated pyoverdine-containing compositions to only some of the plants in the population to cause the insects to avoid other plants in the population to which none the bacteria and/or isolated pyoverdine-containing compositions have been applied. In embodiments, a method pertains to treating only plants in a perimeter of a population to thereby cause the insects to avoid plants in the interior of the population.

The disclosure further includes inspecting at least some of the plants to determine that the plants are insect free or are in contact with fewer insects than a control. The disclosure includes all plants treated with bacteria/compositions as described herein.

In another aspect the disclosure provides a system for use in plant pest control in a confined space, the system comprising a structure for growing plants and one or more light sources that only emit light having a wavelength of 450-525 nm. In an embodiment, the structure comprises a greenhouse, or a hydroponics container for growing plants hydroponically. In a non-limiting configuration, a light source is positioned such that it can illuminate an access point to the greenhouse.

BRIEF DESCRIPTION OF FIGURES

FIG. 10. Graph showing proportion of pea aphids on control plants rather than treated plants in greenhouse experiments. Both immature aphid nymphs and winged adults showed high avoidance of plants treated with Pseudomonas syringae strain B728a.

DETAILED DESCRIPTION

Figure 1:
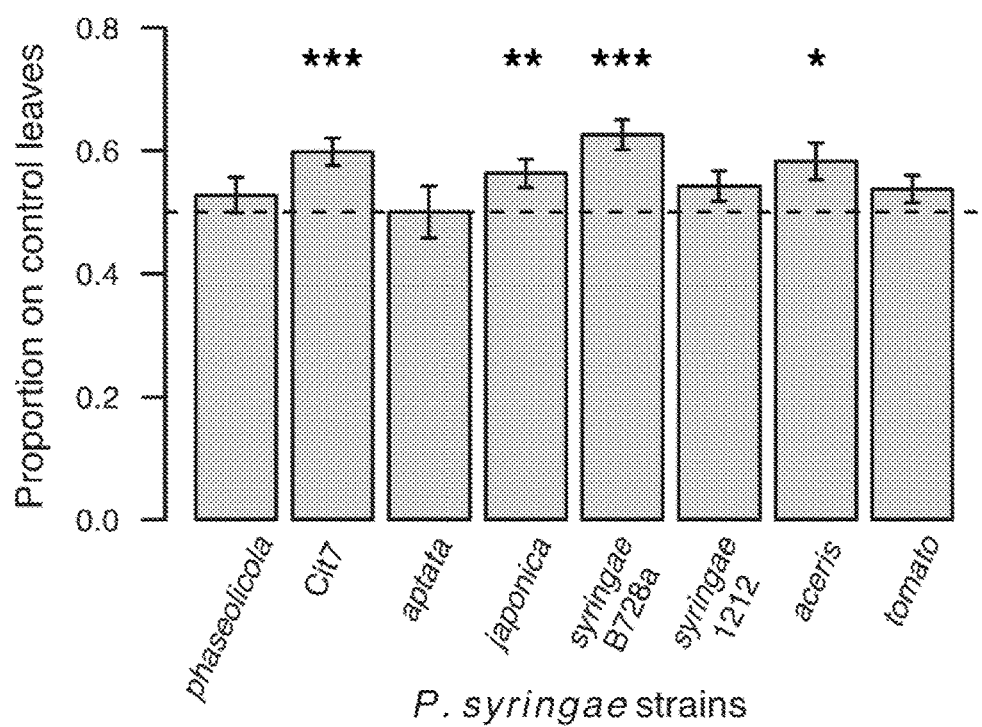
FIG. 1. Pea Aphids Avoid Some, But Not All, *P. syringae* Strains. (A) Avoidance four hours after initial placement on whole plants (GLMM; $\chi^2_7=18.3$, p=0.01). Aphids were able to choose between settling on leaves painted with bacteria or leaves painted with 10 mM $MgCl_2$ buffer solution (control leaves). If aphids have no preference we expect the proportion of aphids on control leaves to be 0.5 (equal to the proportion on leaves with bacteria), whereas a significant increase over that proportion on control leaves indicates significant aphid preference for control leaves over bacterial leaves. The dashed line indicates this avoidance threshold. Those strains where the probability of aphids avoiding bacteria-coated leaves was significantly greater than 0.5 are denoted by asterisks (* p<0.05;  p<0.01; * p<0.001). Sample sizes per strain are as follows: phaseolicola (n=557), Cit7 (n=776), aptata (n=444), japonica (n=552), syringae B728a (n=601), syringae 1212 (n=583), aceris (n=525), and tomato (n=580). (B) Aphid avoidance was positively correlated with the virulence of bacterial strains (One-tailed Pearson's product-moment correlation: t=2.09, df=6, p=0.04, r=0.65). Mean avoidance values are based on results in (A) and virulence means were previously published [9].
Figure 1:
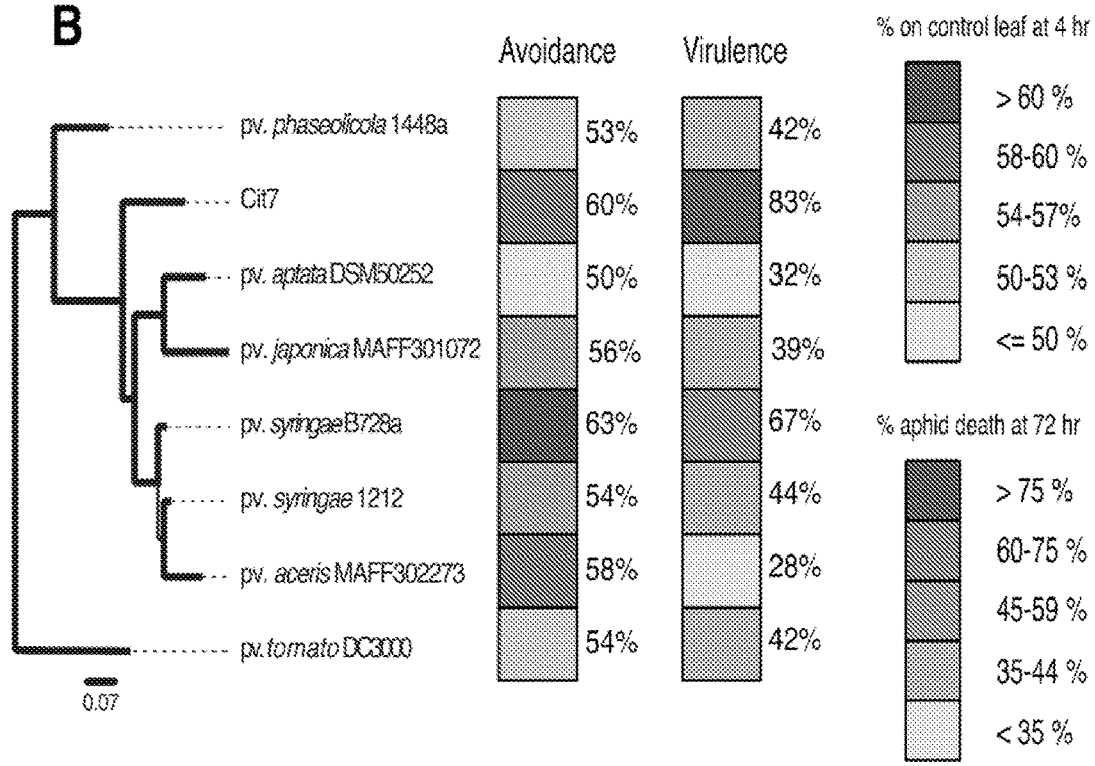

Unless defined otherwise herein, all technical and scientific terms used in this disclosure have the same meaning as commonly understood by one of ordinary skill in the art to which this disclosure pertains.

Every numerical range given throughout this specification includes its upper and lower values, as well as every narrower numerical range that falls within it, as if such narrower numerical ranges were all expressly written herein. The disclosure includes all ranges of wavelength or light, including the upper and lower limits of such ranges, and all numbers and ranges of numbers there between.

In an embodiment, a method of this disclosure comprises controlling insect populations on plants, and particularly on plant leaves. The terms "control" and "controlling" and "controls" are meant to include, but are not limited to, killing, or pestistatic effects, e.g., inhibiting or otherwise interfering with the normal behavior of a pest described herein. These terms also include, for example, disrupting mating or sexual communication, preventing feeding (antifeedant) activity, and/or or promoting avoidance of plants by the pests. In embodiments, controlling insects means promoting their avoidance of plants. In embodiments, insect avoidance achieved by performing a method of this disclosure can be compared to any suitable control to determine if the insects avoid the plants due to application of bacteria and/or a composition described herein. In embodiments, the control comprises plants to which the bacteria and/or the composition has not been applied. In embodiments, the control comprises plants which harbor naturally occurring bacteria that produce a fluorescent siderophore, such as pyoverdine. "Naturally occurring bacteria" means bacteria that are present on plants in an agricultural or horticultural setting, without having been intentionally exposed to the bacteria by human intervention.

In embodiments, when the term "insect" including its plural forms is used it includes aphids.

As is known in the art, aphids are small sap-sucking insects and members of the superfamily Aphidoidea. Common names include greenfly and blackfly. The disclosure includes controlling aphids of any kind that are problematic to plants. In embodiments, the aphids are pea aphids (*Acyrthosiphon pisum*), green peach aphids (*Myzus persicae*), and melon and cotton aphids (*Aphis gossypii*).

In embodiments, the disclosure relates to use of bacteria that produce a fluorescent siderophore that emits light having a wavelength that, as described herein, has now been determined to be the stimulus that causes certain insects to avoid such bacteria, and accordingly to avoid plants that harbor the bacteria. As such, the disclosure includes use of such bacteria, and/or the same or similarly fluorescent siderophores, and/or fluorescent light of the same wavelength, to deter insects from contacting and damaging plants. In embodiments, a suitable wavelength is 450-525 nm, inclusive, and including all ranges of numbers there between.

In certain embodiments, pathogenic bacteria that have been modified to not produce a fluorescent siderophore may be used to, for example, allow aphids come into proximity of the bacteria, and thereby become infected by the pathogenic bacteria, due to the lack of avoidance. In embodiments, bacteria that do not normally produce one or more fluorescent siderophores are modified to produce a suitable fluorescent siderophore and are used in methods of this disclosure.

In embodiments, the disclosure pertains to promoting insect avoidance of plants, and thus in certain implementations is distinct from using bacteria to infect and kill insects, such as aphids. In embodiments, bacteria described herein are applied to plants in an amount that exceeds a particular threshold. In embodiments, the threshold comprises a minimum number of bacteria/unit of plant surface area, such as leaf surface area. Accordingly, in embodiments, the threshold comprises a minimum number of colony forming units (CFU's) per unit of area, CFU's referring to the number of viable bacteria. Thus, and as further described herein, the disclosure reveals for what is believed to be the first time that certain insects, such as aphids, will avoid leaves that have *P. syringae* (or other pyoverdine producing bacteria) present, but only if bacterial density is high enough, and accordingly will not avoid plant leaves that have *P. syringae* (or other pyoverdine producing bacteria) present, but in lower densities. In an embodiment, the disclosure therefore comprises placing bacteria that produce pyoverdine as described herein on plants such that there are at least $10^6$ colony forming units per 3 cm$^2$ on the plants, including but not necessarily limited to plant leaves. In support of this approach, experiments conducted by us demonstrated that a bacterial density of $10^6$ cells per 3 cm$^2$ is sufficient to cause avoidance of plants by aphids. As explained further below, $10^5$ cells per 3 cm$^2$ is not adequate to cause avoidance. In embodiments, the disclosure therefore comprises plants and methods of modifying plant surfaces such that from approximately $10^6$-$10^8$, inclusive, and including all numbers and ranges of numbers there between, bacterial cells per 3 cm$^2$ of area of plant surface are present. In specific a examples, about $5.6 \times 10^7$ cells are present in such a plant area. Measurements of leaf area as described herein include the top and bottom surfaces, but the same bacterial cell density per unit of area can be used on either the top or bottom surfaces. The compositions of this disclosure can, but need not be applied to entire plants, or to entire leaves, or to all of the leaves on a plant or a plant population, provided that at least some of the plants are protected from damage by aphids due to aphid avoidance of the plants facilitated by treatment of the plants as described herein.

It will be recognized by those skilled in the art that the average densities of naturally occurring *P. syringae* populations on plants, such as bean plants, are typically much lower than these values, and commonly around $10^5$ cells per leaf. Thus, the disclosure provides plants that are characterized by having significantly more bacteria described herein on a particular area of the plant than occurs in nature, and furthermore are present in a greater amount in a particular plant area than has been previously described. In embodiments, the disclosure thus provides a method of producing plants that are avoided by insects, and the plants themselves, the method comprising applying bacteria described herein to the plants in an amount such that the insects avoid the area of the plants to which the bacteria have been applied. In embodiments, the bacteria are applied to at least the leaves of the plant. In embodiments, the bacteria are applied to the top, or bottom, or both sides of leaves. In embodiments, the bacteria are applied such that at from 10%-100% of surface the area of a leaf is coated with bacteria at a suitable density to deter insects. In embodiments, some, most or all of the leaves of a plant are coated with bacteria as described herein, and thus from 10-100% of the leaves of a plant have bacteria present on at least their leaves, as described herein. In embodiments, the disclosure includes applying bacteria described herein to plants such that the density of the bacteria exceeds $10^5$ cells on a leaf, and/or is at least $10^6$ cells per 3 cm$^2$, or is about $2 \times 10^6$ cells per 3 cm$^2$, or is about $3.0 \times 10^6$ cells per 3 cm$^2$, or is about $10^7$ cells per 3 cm$^2$ area, or is about $2$-$5 \times 10^7$ cells per 3 cm$^2$ area, or is $10^8$ cells per 3 cm$^2$ area.

Bacterial densities on plants as described herein for promoting insect avoidance are distinct from densities of bacteria to which the insects may be exposed experimentally, such as by feeding, for example, aphids the bacteria in an artificial diet. For example, in embodiments, the disclosure does not pertain to infecting aphids by exposure to bacteria titers in aphid diets, such as a range of $10^2$ CFU ml$^{-1}$ to $10^9$ CFU ml$^{-1}$ in for example, 200 µl of artificial aphid diet. Thus, bacterial concentration on a plant surface as described herein is fundamentally distinct from directly infecting aphids with bacteria by manipulating artificial diets, as described in Hendry et al., R. Soc. open sci. 3:150478 (2016).

In certain embodiments, the disclosure includes any one or any combination of the following provisos. In embodiments, any composition described herein may be free of oil, including but not limited to vegetable oil and unsaturated fatty acids and or a derivatives thereof. In embodiments, any composition of this disclosure may be free of any seed extract, including but not limited to *cuminum cyminum*. In embodiments, any composition may comprise or consist of a particular species, type or strain of bacteria described herein, and therefore the bacteria that is applied to the plants may be the only type of bacteria applied to the plants, and is sufficient to achieve a result described herein. In embodiments, a bacterial population applied to plants does not contain any *B. burgdorferi*. In embodiments, bacteria applied to plants according to this disclosure are not microencapsulated, and/or are not fermenting bacteria, or are not in a state of fermentation. In embodiments, performing a method of this disclosure does not deter any type of moth from contacting the plant. In embodiments, a method of this disclosure is not performed to reduce a bacteria or fungal infection of a plant. In embodiments, the composition is not used to treat or prevent bacterial blight, such as of passion fruit.

In embodiments, a composition of this disclosure is applied to aphid-free plants. In embodiments, subsequent to applying a composition to plants as described herein, an inspection of plants that received the composition can be made in order to confirm efficacy insect deterrence, or, if the application did not result in adequate deterrence, the disclosure comprises changing the amount of effective agents in the composition.

In embodiments, a composition of this disclosure is applied to plants in an environment where there is no or low risk of ice crystal formation, such as in a controlled environment or consistently warm geographic region, or is applied only during a seasonal period wherein risk of ice crystal formation is low or non-existent. In embodiments, the bacteria do not exhibit an ice nucleation deficient phenotype.

Applications of the bacterial and/or pyoverdine compositions described herein are not limited to any particular type of plants, or environment. In embodiments, the plants are any leafy plant. In embodiments, the plants are any agricultural or horticultural plants. In embodiments, an agricultural plant comprises any grain plants, fruit plants vegetable plants, and flowering and foliage plants and trees. In embodiments, the plant is any annual plant. In embodiments, the plant is any perennial plant, including but not limited to herbaceous perennials, perennial bedding plants, and container plants. In embodiments, the plants are ornamental plants. In embodiments, the plant is selected from ageratum, alyssum, celosia, chrysanthemum, dahlia, gerbera daisy, herbs (many types), fuchsia, hydrangea, impatiens, pansy, pepper, portulaca, primula, salvia, snapdragon, tomato, verbena and zinnia. In embodiments, the plant is intended for human or non-human animal consumption, non-limiting examples of which pea plants, sugar cane, wheat, sorghum, rice, corn, potato, sugar beet, barley, sweet potato, cassava, soybean, grapes, tomato, banana, beans and peas, cabbages, lettuces, cruciferous vegetables, cucumbers, melons, apple and citrus plants, such as orange grapefruit trees. In one embodiment, the plants are cannabis plants. In another embodiment, the plants are cotton plants.

In embodiments, the disclosure facilitates inhibition of vectoring of plant viruses by insects.

Compositions of this disclosure can further comprise other anti-arthropod agents, including but not necessarily limited to synthetic chemical insecticides (larvicides, adulticides, ovicides), acaricides (miticides), fungicides, nematicides, parasiticides, or other control agents.

In embodiments, a method of this disclosure is combined with any other suitable approach to insect control, including but not limited to foliar and granular applications of insecticides, non-limiting examples of which include thiamethoxam disulfoton, disyston, phorate, dithiodemeton, dimethoate, telodrin, endosulfan, Demeton-S-methyl, disulfoton, monocrotophos, parathionmalathion, carbofuran, carbophenothion, demeton, endrin, endosulfan, phoratediazinon, Meta-Systox, phosdrin, and quinalphos.

The bacteria that are used in methods of this disclosure are not particularly limited, other than a requirement to produce adequate amount of a fluorescent siderophore such that insects as described herein avoid the plants. In embodiments, the bacteria is any member of the Pseudomonadaceae family, and is thus any fluorescent siderophore-producing pseudomonad. In embodiments, the bacteria is *P. fluorescens*, or *P. syringae*. The disclosure includes all types and strains of *P. syringae* described herein.

In embodiments, a composition of this disclosure comprises a suitable fluorescent siderophore, as demonstrated herein using pyoverdine. The chemical structure of pyoverdine is known in the art, and is commercially available. Pyoverdine has a molecular formula of $C_{56}H_{88}N_{18}O_{22}$ and a molar mass of 1,365.42 $g \cdot mol^{-1}$. In embodiments, the pyoverdine has a dihydroxyquinoline core that is comprised of (1S)-5-amino-2,3-dihydro-8,9-dihydroxy-1H-pyrimido[1,2-a]quinoline-1-carboxylic acid. The genes required for biosynthesis of pyoverdine are known in the art.

In certain implementations, modified bacteria are provided and produce the pyoverdine such that they produce the pyoverdine via expression of one or more genes and/or a promoter that has been introduced to the bacteria.

In embodiments, the disclosure provides a pesticidal composition comprising an effective amount of bacteria that are pathogenic to the insects, wherein at least some of the bacteria have been modified, such as to not produce pyoverdine or to produce less pyoverdine relative to unmodified control bacteria, and/or have been rendered non-pathogenic to the insects but have modified production of pyoverdine. Thus, in certain embodiments, the bacteria that are pathogenic to the insects are used, and have been modified by disrupting one or more genes that encode proteins that participate in synthesis of pyoverdine in the bacteria. Techniques for modifying bacteria are known in the art and can be readily adapted for use in embodiments by the skilled artisan, given the benefit of this disclosure.

The disclosure also includes one or more bacterial cultures that comprise modified bacteria described herein, cell lysates from such bacteria, and the modified bacteria themselves.

In another aspect the disclosure provides a composition comprising isolated pyoverdine (which may further comprise any bacteria described herein) for use in reducing an amount of insects on plants, wherein the composition comprises at least one agent that promotes persistence of the pyoverdine on the plants, relative to persistence on the plants of a composition comprising the isolated pyoverdine that does not comprise the at least one agent. Such agents can include but are not necessarily limited to glycerin, smectite clays, attapulgite clays and similar swelling clays, thickeners such as gums and polysaccharide thickeners, as well as dispersion stabilizers such as nonionic surfactants. The compositions can comprise emulsions, suspensions, dispersions, and the like. In embodiments, the compositions are non-systemic, meaning they do not penetrate the leaf cuticle, and/or are not taken up into plant tissue after application. In embodiments, isolated pyoverdine is pyoverdine that is provided as a composition, apart from being a component of intact bacterial cells. In embodiments, the pyoverdine is purified to any desired degree of purity. In embodiments, the pyoverdine is separated from bacterial cells. In embodiments, the pyoverdine is present in bacterial cell lysates. In embodiments, we demonstrated that pyoverdine concentration of 0.001 mg/mL is a minimum concentration necessary to cause avoidance. Thus, approximately 0.00005 mg on a 3 $cm^2$ portion of the leaves is considered to be sufficient for avoidance. Therefore, concentrations at or above 0.0005 $mg/3\ cm^2$ of leaf are sufficient for avoidance and are encompassed by this disclosure.

In an embodiment, an effective amount of a composition is used. An effective amount means an amount of a composition and/or bacteria described herein that is suitable for obtaining an intended result, i.e. preventing infestations of plants by the pests, repelling and/or killing such pests. Suitable amounts (e.g., densities) of bacteria are described herein. In embodiments, a combination of modified bacteria and/or isolated pyoverdine results in synergistic reduction in insects present on plants.

In embodiments, the disclosure comprises applying a bacteria described herein and/or a composition comprising one or more fluorescent siderophores to only some plants in population of plants to cause the insects to avoid other plants in the population to which neither the bacteria or the composition has been applied. Thus, for example, the bacteria and/or the composition may be applied only to plants on a perimeter of a plant population, such as a crop, or plants near points of a confined environment, such as a greenhouse, where insects may gain access to the plants. Alternatively, only some plants within a population of plants can be treated using the bacteria and/or other compositions described herein.

Compositions of this disclosure can be applied to plants using any suitable technique and/or device, and include but are not necessarily limited to immersion, spraying, evaporation, fogging, scattering, and painting.

In embodiments, the disclosure includes applying the bacteria and/or a composition described herein to insect-free plants.

In embodiments, the disclosure includes applying the bacteria and/or a composition described herein to plants that are in a confined environment. In embodiments, the confined environment comprises a structure. In embodiments, the structure is a greenhouse. Any suitable greenhouse is included within the scope of the disclosure. As is known in the art, a greenhouse is greenhouse, which includes so-called glasshouses and if heating is provided, a hothouse, is a structure with walls and roof made primarily of transparent material, such as glass, in which plants that require regulated climatic conditions are grown. In embodiments, the confined space is a hydroponics system. A hydroponics system is a confined environment wherein the process of growing plants in sand, gravel, or liquid, with added nutrients but without soil, is performed. In embodiments, systems and methods of this disclosure comprise a confined space and one or more artificial light sources, which are generally electric lights, which may emitting a light that can deter insects as further described herein. In embodiments, the lights are high Intensity Discharge (HID) lights, or metal halide lights or ceramic metal lights, or are light-emitting diodes (LEDs), including organic light emitting diodes (OLEDs). The light may be tailored such that it emits light only in a wavelength of 450-525 nm, or a light that is a wider spectrum may be adapted to produce light with a wavelength of 450-525 nm using any of a variety of filters. The light may have any suitable wattage, including but not limited to 150 W, 250 W, 400 W, 600 W and 1000 W. In embodiments, a mixture of electronic lights, such as a mixture of various types of LEDs, each producing a specific portion of the desired light spectrum, is used. Thus, an array of LEDs configured to both promote photosynthesis and insect avoidance can be provided. Accordingly, a grow light comprising an array of LEDs or any other electronic light source is provided and produces light in a variety light spectrums, but is designed to enhance emission of light in the wavelength of 450-525 nm. In embodiments, the disclosure accordingly provides a confined environment in a structure, such as a greenhouse and/or hydroponics system, comprising a confined environment for housing and growing plants; and one or more electronic lights as described above. In a greenhouse setting, for example, the lights can be provided within or near access points to the greenhouse, although the same approach can be used for hydroponics systems. The system may also comprise any suitable power source, and optionally one or more timers, and optionally one or more sensors for measuring one or more variables which are directly or indirectly related to growth, development or health of the plants, and/or the presence of insects, and any suitable control apparatus arranged to control illumination from the modular the electronic light(s). The system may further include a processor to control an amount of electrical current supplied to the electronic lights, so that a particular amount of current determines a color of light generated by, for example, one or more LEDs. In such embodiments, controlling the amount of electrical current supplied to the plurality of LEDs or other light source can affect the color of light generated by the plurality of LEDs. In embodiments, approximately 10-100% of the light produced by the electronic light is a wavelength of 450-525 nm. In embodiments, the one or more electronic lights are positioned so that some or all of the plants within the system receive the desired light. Alternatively or in addition to positioning the light(s) within system, one or more lights may be positioned such that light is produced to illuminate the access point(s), and thereby deter insects from passing through the access point when it is open, such as in the case of a greenhouse, for when a human greenhouse attendant is entering or exiting the greenhouse, or when the access point is opened for any other reason. In embodiments, the light illuminates one or more vents. In embodiments, the light is produced only during certain periods, such as during periods during which light comprising the full visible spectrum is not provided. In embodiments, kits for assembling a structure such as a greenhouse and/or a hydroponics system comprising a light source described herein are provided.

The following Examples are intended to illustrate but not limit the disclosure. The following Examples provide representative demonstrations using aphids. Aphids are diverse sap-sucking insects [1] that can be serious agricultural pests and vectors of plant disease [2]. Some species, including pea aphids (*Acyrthosiphon pisum*), are susceptible to infection by epiphytic bacteria commonly found on plant surfaces [3-5]. Pea aphids appear unable to recover from these infections, possibly because pea aphids are missing apparent orthologs of some immune response genes [6], and these aphids exhibit relatively low immune responses after pathogen exposure [7]. We therefore tested the ability of pea aphids to use avoidance as a non-immunological defense against *Pseudomonas syringae*, which is known as a widespread plant epiphyte and aphid pathogen [8, 9]. The results demonstrates that pea aphids avoided highly virulent strains of *P. syringae*, but not all strains, and avoidance led to a significant reduction in infection among aphids. We found that aphids can use visual cues to detect the ultraviolet (UV)-based fluorescence of the bacterial siderophore pyoverdine [10] produced by virulent strains. Avoided epiphytic bacteria caused light leaving the surface of leaves to be richer in wavelengths that were tightly linked to both aphid visual sensitivities and the fluorescent emission spectra of pyoverdine, indicating that pyoverdine fluorescence mediates avoidance and may be a visual cue used by aphids to detect epiphytic pathogens. Although pyoverdine production in *Pseudomonas* species and may be a broadly reliable indicator of bacterial virulence within the phyllosphere, it was not directly responsible for virulence to aphids. Aphids may be under selection to avoid fluorescence on leaves, a phenomenon with use for control of agricultural pest insects, as described above.

Example 1

Avoidance of Virulent Bacteria

Epiphytic bacteria can be highly infective and virulent to pea aphids [3-5, 9, 11, 12]. For instance, *P. syringae* strains can cause death with fewer than ten cells ingested [13], and infect up to 30% of individuals on a plant [11]. Infected individuals may die in as few as four days and do not appear able to recover from infections [13]. Evidence suggests that aphids may use non-immunological defense strategies against such pathogens. These include: symbiont-mediated immunity, where symbionts protect against pathogens [14, 15]; fecundity compensation, where individuals increase reproduction after infection [13]; or avoidance [16]. Given the high infectivity, virulence, and incidence of potential bacterial pathogens on plants, we analyzed whether the ability to detect and avoid these pathogens in the phyllosphere before exposure is beneficial to aphids, and therefore be selected for, and have adapted the results presented here to arrive in part at the present disclosure.

In more detail, we performed experiments using multiple strains of *P. syringae* that varied in virulence to pea aphids. We observed the preference of aphids given a choice between leaves with or without epiphytic bacteria. Additionally, we sought to determine which cues aphids used to detect the presence of bacterial pathogens.

Figure 5:
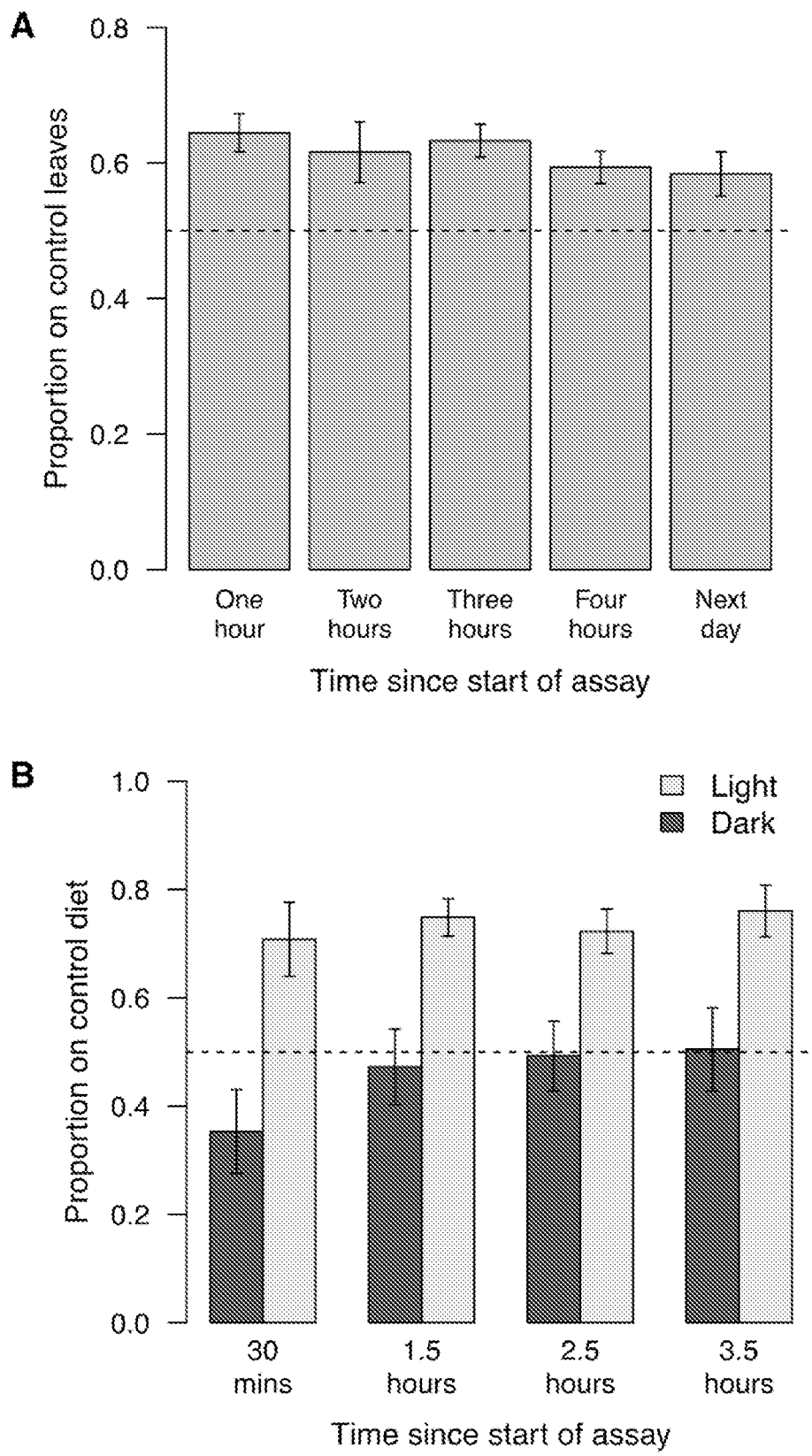
FIG. 5. Aphid Preference and Feeding Over Time and Light Conditions, related to FIG. 2. (A) Aphid preference for control leaves versus leaves with epiphytic Psy B728a over time. (B) Aphid feeding preference over time for control artificial diet versus Psy B728a cells suspended in artificial diet, under normal light and dark conditions. (C) Aphid feeding preference over time in the dark. Included is the total number of aphids on both control and bacterial leaves. (D) Aphid feeding preference over time under UV-blocking plastic. Included is the total number of aphids on both control and bacterial leaves.
Figure 5:
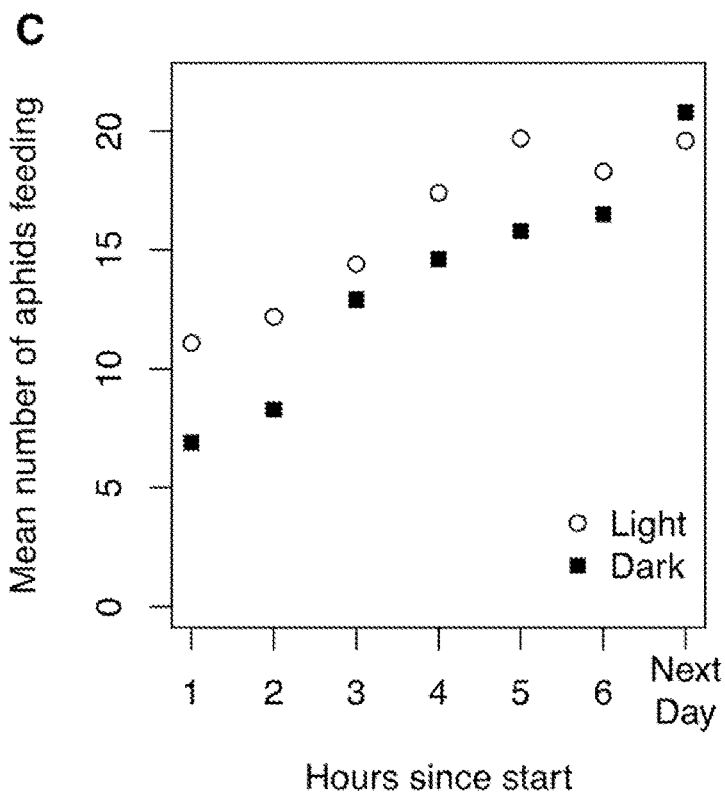
Figure 5:
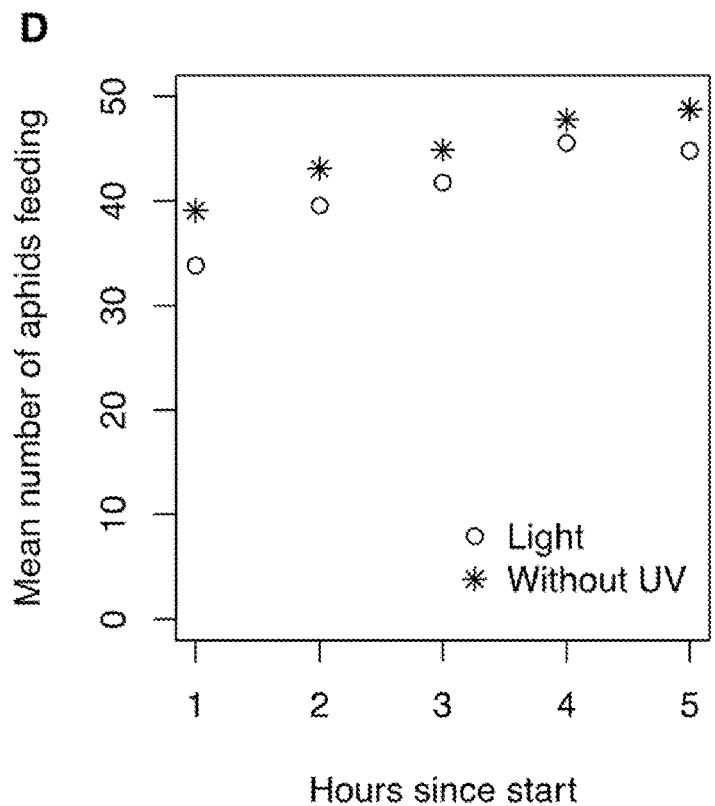
Figure 6:
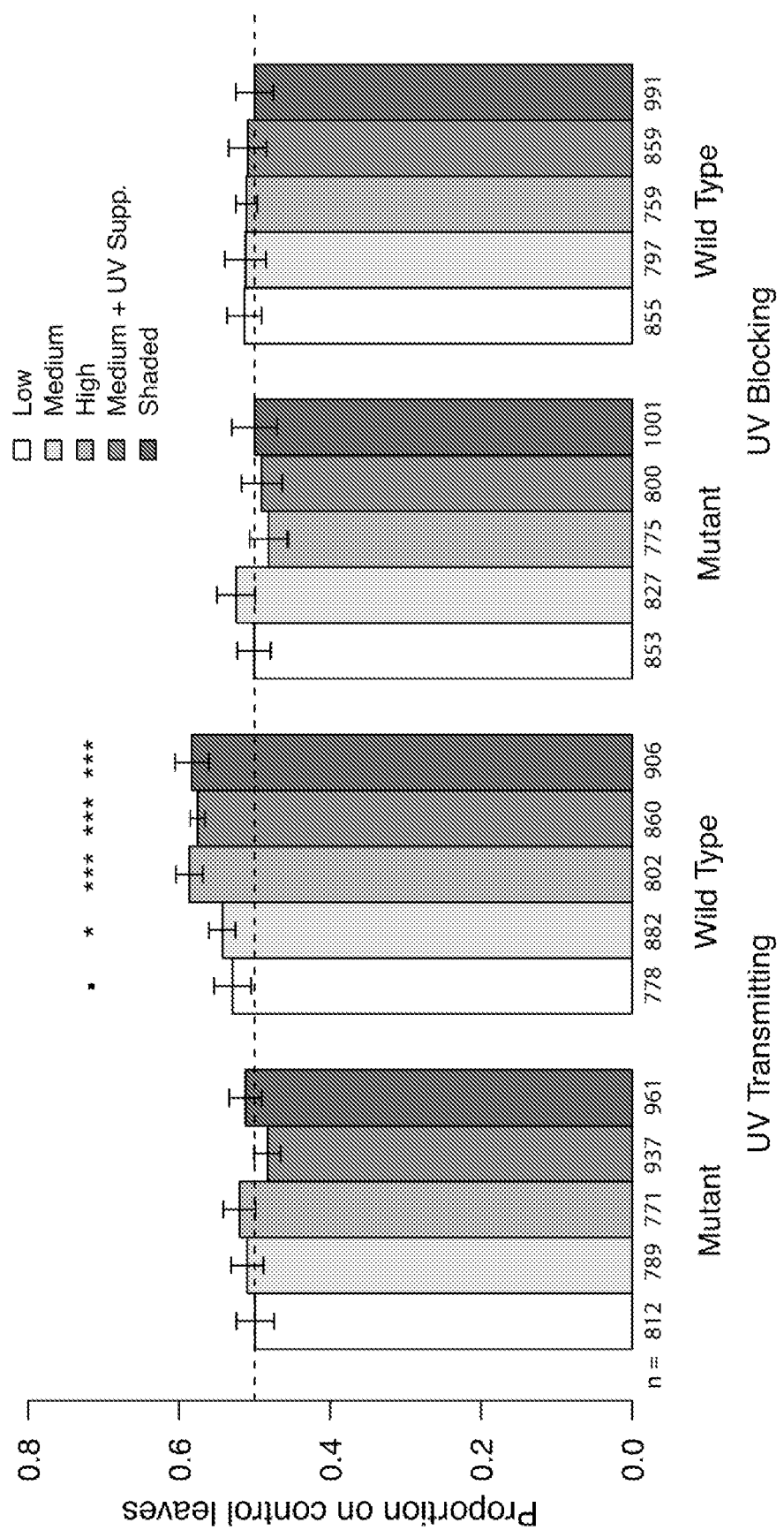
FIG. 6. Levels of UV Light Influence Avoidance of Pyoverdine Producing Bacteria, related to FIG. 2. Choice assays between leaves with wild type Psy B278a and control leaves or leaves with a pyoverdine-deficient mutant and control leaves, performed on excised leaves under UV transmitting or UV blocking plexiglass. Four hours after the start of the assay, aphids significantly preferred control leaves over leaves with wild type Psy B278a under medium, high, and shaded (high but indirect light) lighting conditions only when UV light was present (GLMM of plexiglass 'type': $\chi^2_1$=24.68, p<0.001). UV supplementation of medium lighting increased avoidance to the same level as under high light. Neither plexiglass type nor brightness level affected aphid preference for the pyoverdine-deficient mutant. Samples sizes are shown under the bars and those strains where the probability of aphids avoiding bacteria-coated leaves was significantly greater than 0.5 are denoted by asterisks ($\square$ p<0.1; * p<0.05; *** p<0.001).
Figure 7:
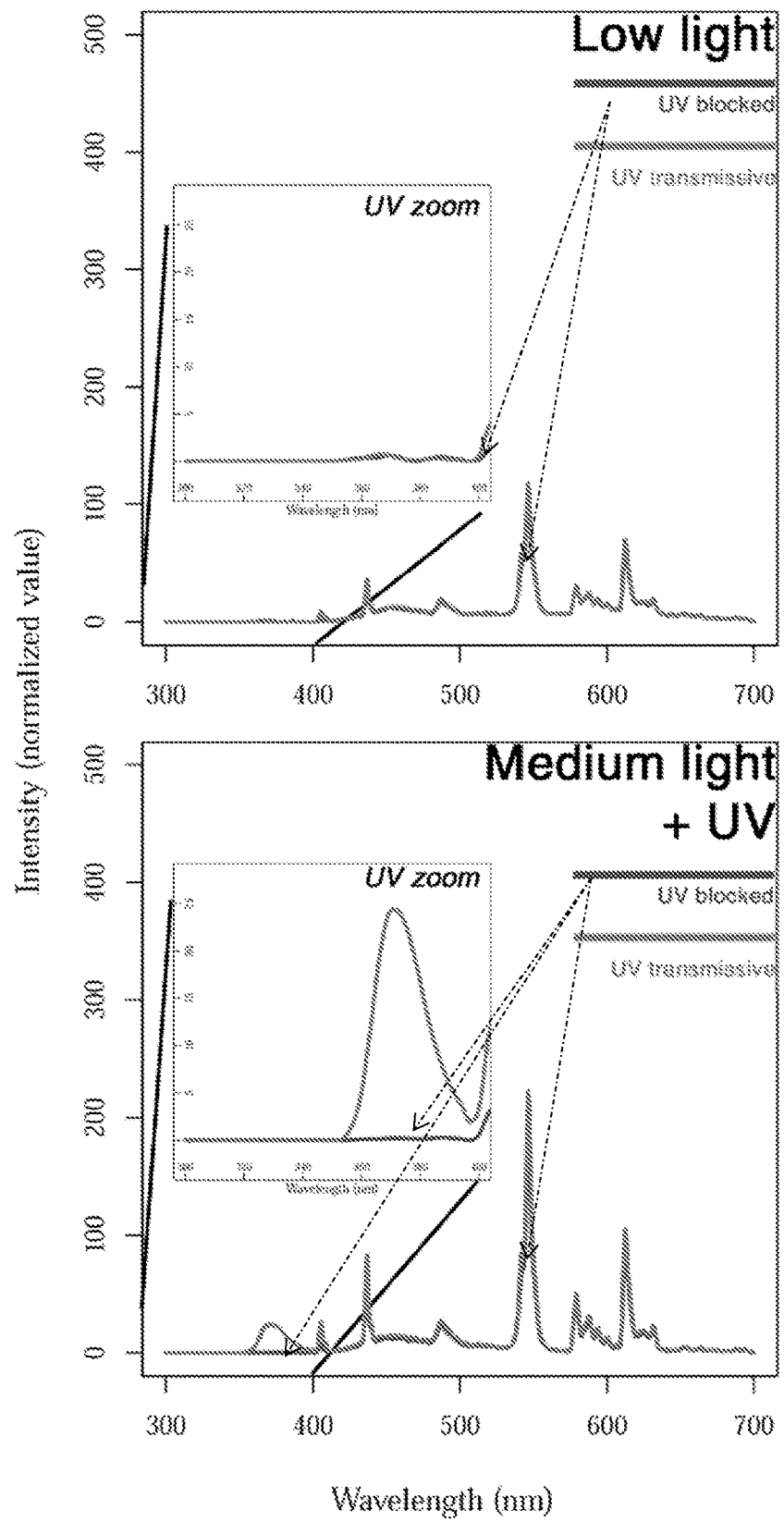
FIG. 7. Irradiance Spectra of Experimental Lighting Conditions, related to FIG. 2. Irradiance spectra of low, medium, medium+UV, and high light conditions used during experimental assays of visually-mediated avoidance behavior of aphids. These lighting conditions were used in the experiments shows in FIG. 6.
Figure 7:
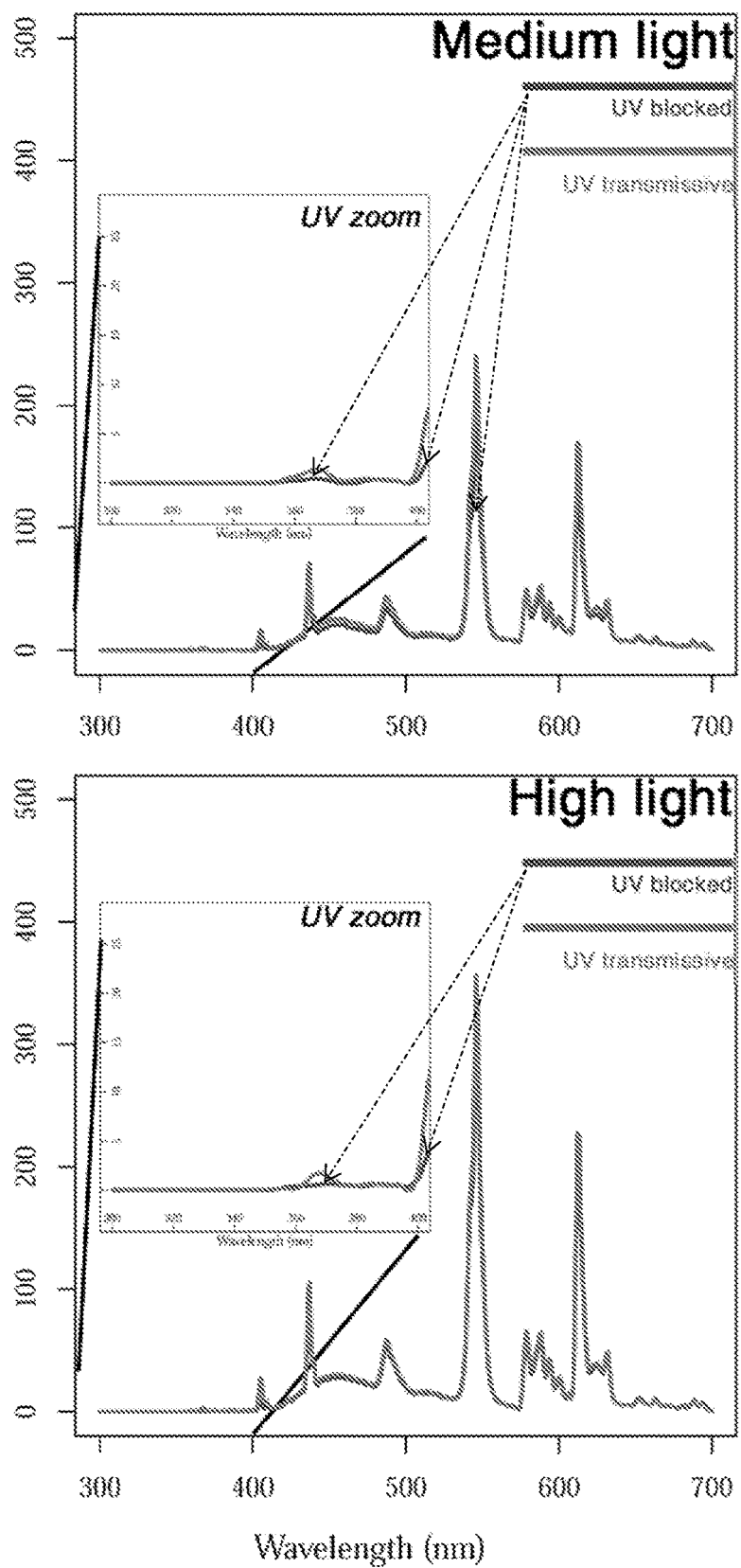

In choice assays on plants, aphids significantly avoided some, but not all, epiphytic *P. syringae* strains (FIG. 1A). Individual leaflets within fava bean (*Vicia faba*) leaf pairs were painted with either a control solution or bacterial suspension. Pea aphids were introduced at the base of the plant and observed daily. The majority of aphids settled to feed on a leaf within a few hours and numbers feeding on leaves stayed relatively constant for several days (FIG. 5A). Many bacterial strains elicited no significant difference in the numbers of aphids feeding on control leaves versus leaves with bacteria. Some bacterial strains, however, caused aphids to significantly avoid leaves. For instance, on average the strains *P. syringae* pv. syringae B278a (referred to as Psy B728a for ease) and *P. syringae* Cit7 caused 65% and 60% of aphids to choose control leaves after four hours on plants, with up to 81% of aphids preferring control leaves on some plants treated with Psy B728a. Without intending to be constrained by any particularly theory, these two strains are thought to be representative of strains that persist well epiphytically [17, 18], demonstrating that common epiphytic bacteria can decrease the likelihood that aphids will feed on leaves.

Aphid avoidance was positively correlated with the virulence of strains to aphids (FIG. 1B, One-tailed Pearson's product-moment correlation: t=2.09, df=6, p=0.04, r=0.65), suggesting that avoidance may benefit aphids by decreasing their risk of infection by deadly bacteria. Supporting this, we found that aphids with a choice between control and bacterial leaves had lower infection rates than when all available leaves were painted with virulent bacteria (5% vs. 14% infected respectively; GLMM; $\chi^2_1$=6.04, p=0.01, n=240), despite both treatments having equal numbers of leaves painted with bacteria. Aphids avoided all strains previously shown to be highly virulent [9], but some strains were avoided disproportionately for their virulence, suggesting that aphids may overestimate but not underestimate the virulence of a strain. However, it was initially unclear how aphids are able to make these discriminations. This effect is unlikely to be plant-mediated because many aphids chose control leaves within an hour of bacteria being placed on plants, giving fairly little time for the bacteria to elicit a plant defense response (FIG. 5B).

Example 2

Visual Detection of Bacterial Pathogens

Figure 2:
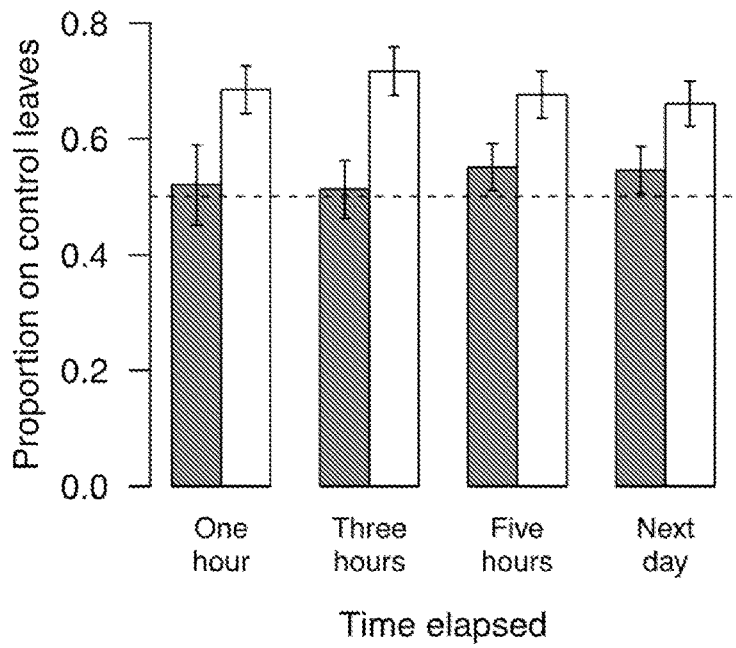
FIG. 2. UV Light is Necessary for Aphids to Avoid Virulent Strains. (A) Avoidance of the highly virulent strain Psy B278a was dramatically reduced when choice experiments were conducted in the dark (GLMM: $\chi^2_1=28.55$, p<0.001) as aphids no longer avoided the leaves painted with bacteria (probability of avoiding bacterial leaves in the dark: p=0.54, 95% CI=0.43–0.64). Time elapsed since the start of the experiment had no effect on the aphids' choice whether in the dark or normal light (GLMM: $\chi^2_3=2.03$, p=0.57). Experiments were done with excised leaves and total number of aphids (n) of n=208 for the dark treatment and n=196 for the normal light treatment. (B) This result was mirrored when choice experiments were then conducted under UV blocking plastic as compared to normal light (effect of UV block: GLMM: $\chi^2_1=37.90$, p<0.001; probability of avoiding bacterial leaves under UV block: p=0.52, 95% CI=0.49–0.55). Again, aphid choices did not change over time in either treatment (GLMM: $\chi^2_2=0.85$, p=0.65). Experiments were done with excised leaves and n=737 aphids for the UV block treatment and n=664 aphids for the normal light treatment.
Figure 2:
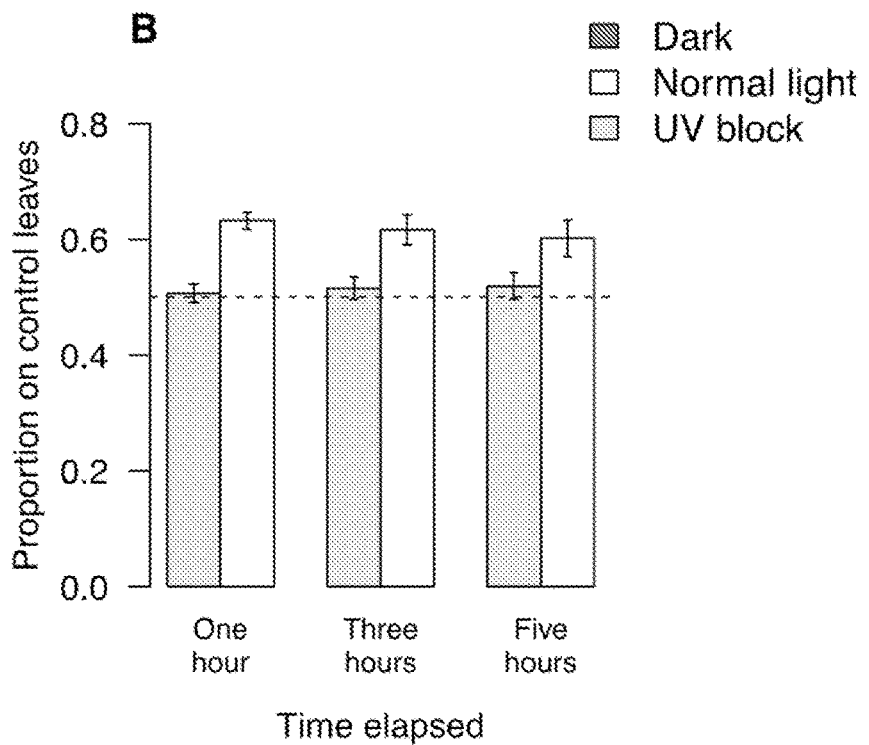
Figure 3:
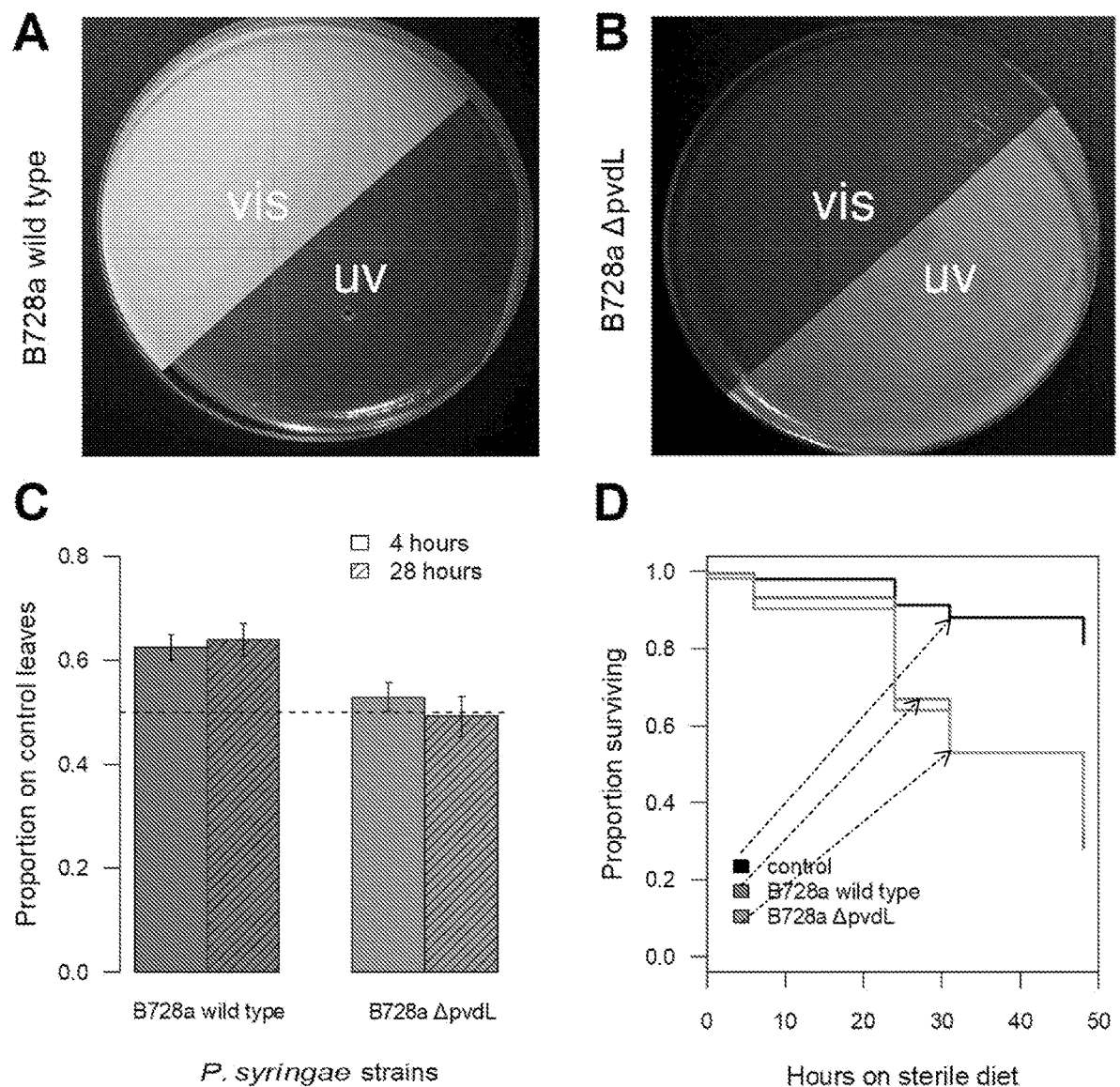
FIG. 3. Pyoverdine Production by Virulent Bacteria is Necessary for Avoidance But Does Not Kill Aphids. (A) Composite black-light illuminated photographs capturing human-visible (vis) and ultra-violet (uv) wavelengths of light illustrate that the wild-type bacterial strain Psy B278a which is avoided by aphids is highly fluorescent (vis) as a consequence of the conversion of short-wavelengths of ultraviolet light (uv) being absorbed and re-emitted as longer wavelengths of light. (B) Conversely, the pyoverdine-deficient mutant of this strain has little/no fluorescence in the human-visual portion of the electromagnetic spectrum (vis) and, correspondingly high levels of reflectance in the ultra-violet (uv). Both (A) and (B) are composite images of bacterial lawns growing on King's B agar plates, illuminated with UV light and photographed using a modified Canon 7D camera with either a 400 nm-690 nm Baader filter (left), or a UV only Baader filter (right). (C) Knocking out pyoverdine production led to a loss of avoidance in comparison to the wild type (wild type vs. mutant GLMM: $\chi^2_1$=45.37, p<0.001; probability of avoiding mutant: p=0.51, 95% CI=0.48-0.54). These assays were performed on whole plants with n=1250 aphids for mutant treatments and n=1205 aphids for wild type treatments. (D) Pyoverdine production did not influence the virulence to aphids (log rank test of Kaplan-Meier survival curves: $\chi^2_1$=0.50, p=0.46, n=384 aphids exposed to wild type, n=670 aphids exposed to the mutant, and n=479 control aphids).

An important part of the aphid life cycle is dispersal: finding and discriminating among potential host plants, and ultimately settling to feed. Aphids rely heavily on visual information in finding and selecting host plants [19]. To test if aphids could use visual cues to avoid potential pathogens we compared behavioral avoidance of strain Psy B728a in the dark with avoidance under normal lighting conditions. In the dark, aphids were no longer able to distinguish between control and bacterial leaves and showed no significant preference, compared to aphids under normal light conditions (FIG. 2A, light vs. dark GLMM: $\chi^2_1$=28.55, p<0.001; probability of avoiding bacterial leaves in the dark: p=0.54, 95% CI=0.43-0.64). Again, this response is likely not plant-mediated, as similar avoidance patterns under normal light or dark conditions were seen in the absence of plants when experiments were performed using bacteria suspended in artificial aphid diet (FIG. 5B). This result is also not driven by altered feeding rates under different conditions, as feeding rates in the dark did, after a slight lag, match rates under normal light (FIG. 5C). These findings demonstrate that aphid vision plays a role in detecting virulent epiphytic bacteria.

Aphids are known to respond differentially to different wavelengths of light [20], and because a common feature of many *Pseudomonas* species is that they produce fluorescent compounds that absorb ultraviolet (UV) light and emit visible light [21], we sought to determine if virulent bacteria could be altering the appearance of leaves due to fluorescence and if aphids could therefore visually detect the presence of bacteria. We repeated choice assays under UV blocking plastic, using strain Psy B728a, which was highly avoided under normal lighting conditions. Without the presence of UV light, aphids no longer avoided leaves with these epiphytic bacteria (FIG. 2B; light vs. UV block GLMM: $\chi^2_1$=37.90, p<0.001; probability of avoiding bacterial leaves under UV block: p=0.52, 95% CI=0.49–0.55). Again, this result was not an artifact of decreased feeding rates, as aphids actually fed at higher rates without UV light (FIG. 5D). These findings demonstrate that avoidance requires UV light and suggests that avoidance behavior could be dependent on fluorescent molecules produced by *P. syringae*.

Example 3

Pyoverdine Mediates Pathogen Detection

Figure 8:
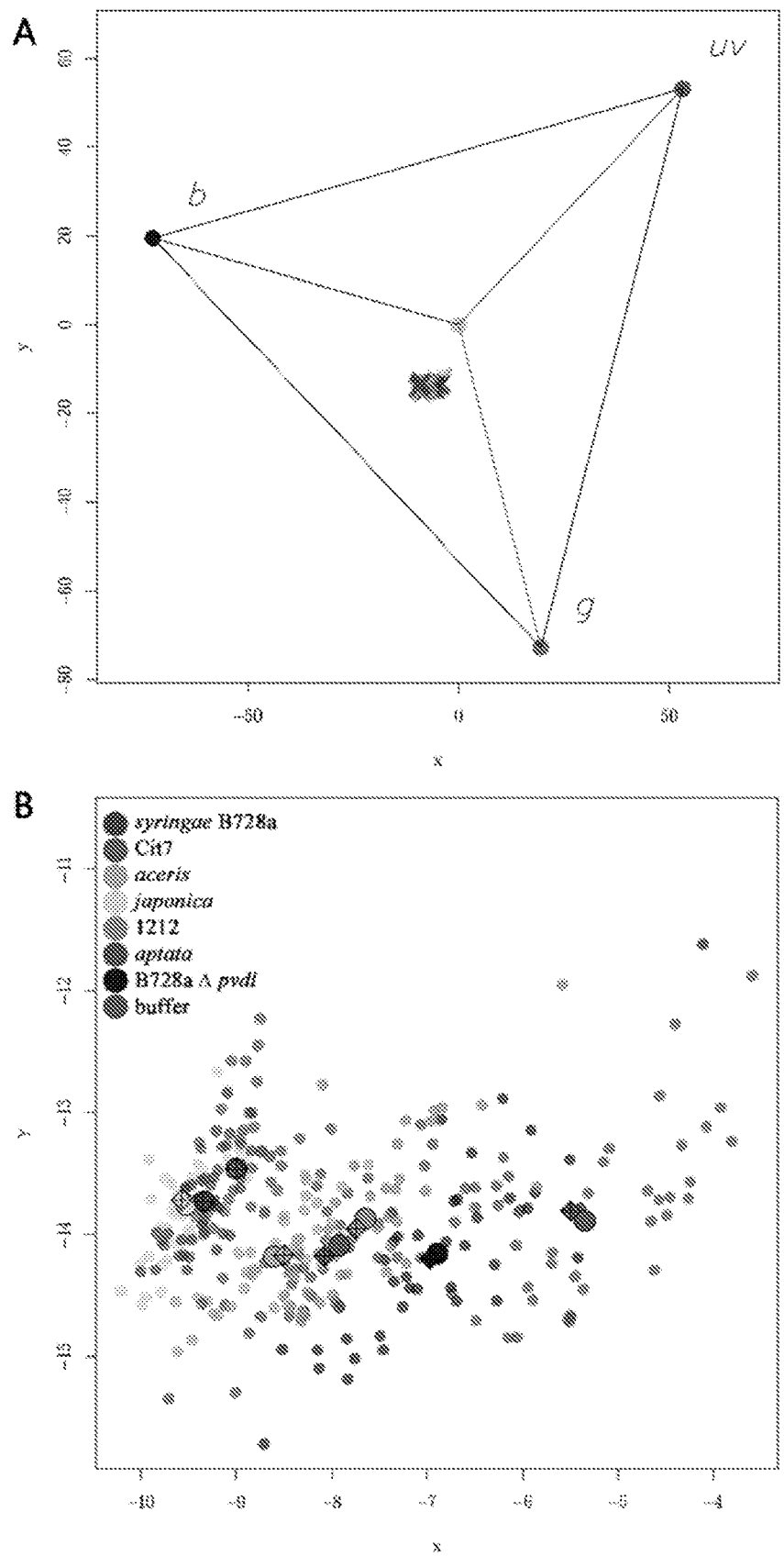
FIG. 8. Visual Modeling Indicates that Avoided Bacteria are Visually Distinctive to Aphids, Related to FIG. 4. Visual models of a closely related aphid species indicate that leaves with epiphytic bacterial strains that are avoided look different to aphids as a consequence of fluorescence-induced shifts in excitance. (A) The vertices (uv, b, g) in the trichromatic, aphid color space diagram (with gray, achromatic center) correspond to maximal stimulation of the three different photoreceptor types and illustrate the relative location of leaves in aphid colorspace (blue-green). (B) Zoomed in view of the measurements within aphid colorspace, where individual points correspond to individual measurements, large circles correspond to mean values, and diamonds correspond to median values. Each color measurement can be evaluated based on its chroma (i.e. its distance from the achromatic center) and hue (angle $\theta$) relative to the achromatic-UV vector (purple line in A).
Figure 9:
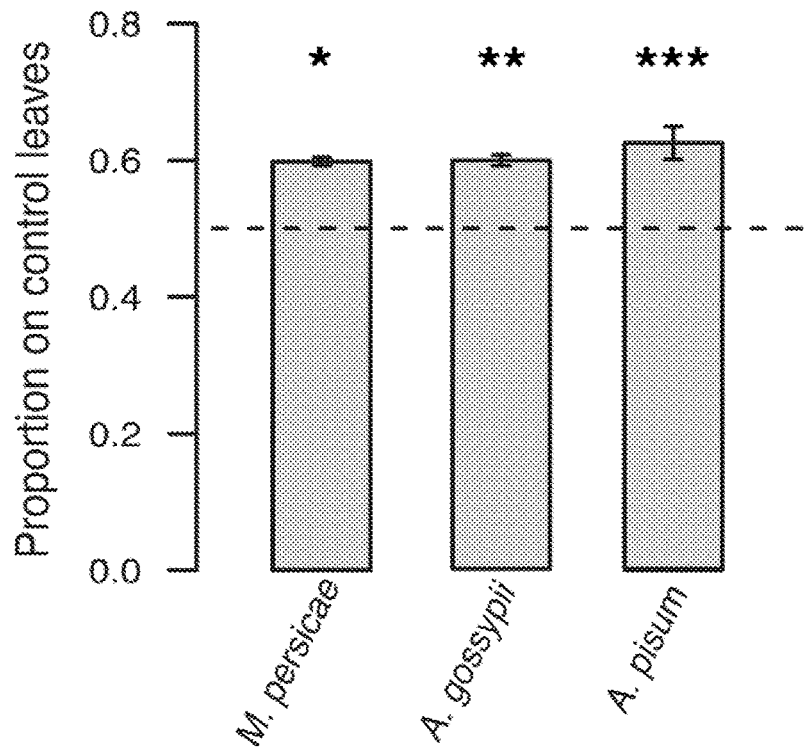
FIG. 9. Graphs showing proportion of aphids on control leaves rather than treated leaves across aphid species. Three species of aphid avoid the virulent Pseudomonas syringae strain B728a: Myzus persicae, Aphis gossypi, and Acyrthosiphon pisum.
Figure 10:
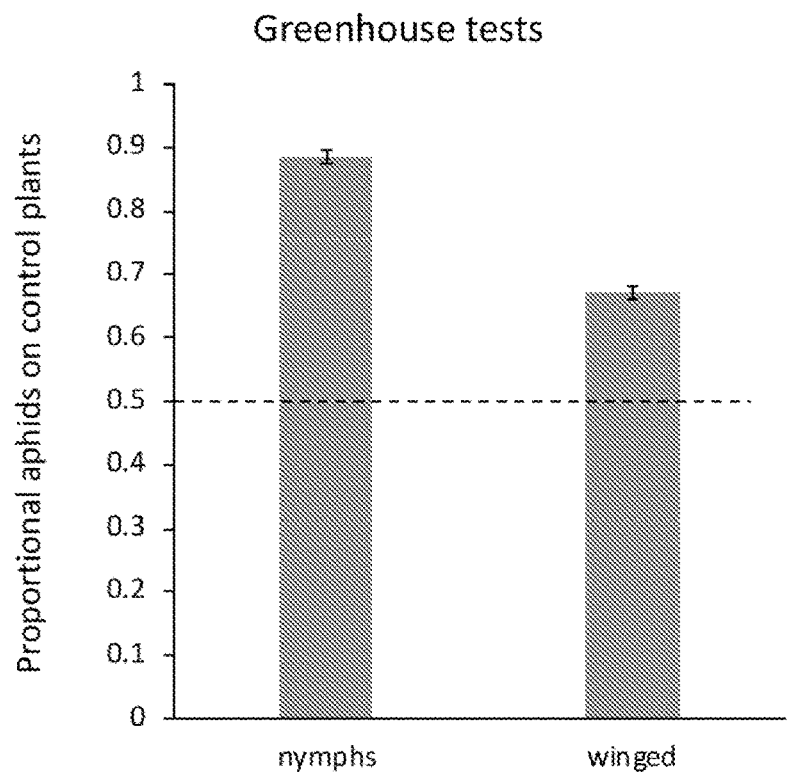
Figure 11:
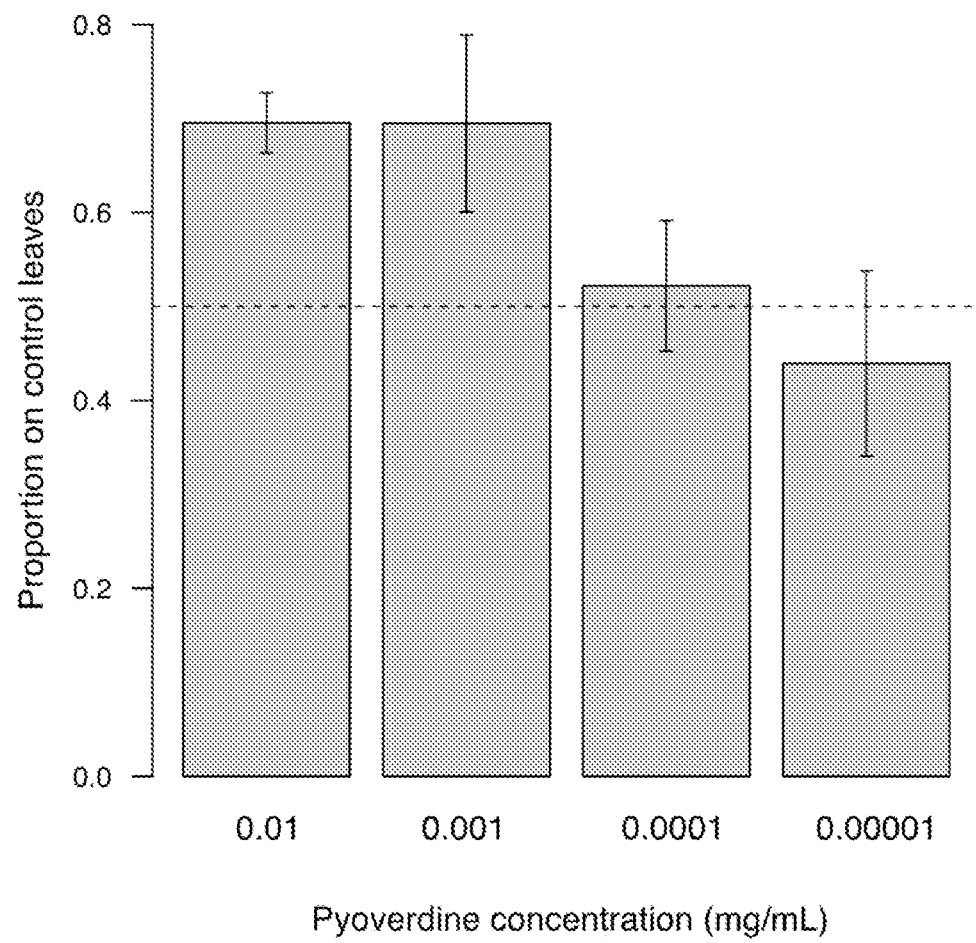
FIG. 11. Graph showing pea aphid avoidance of purified Pseudomonas fluorescens pyoverdine on leaves. Varied concentrations of pyoverdine were applied to leaves and aphids were given a choice between a treated leaf and a control. At concentrations of 0.001 mg/mL and above aphids significantly preferred control leaves to treated leaves. Purified Pseudomonas fluorescens pyoverdine was diluted it in sterile water and applied to leaves and aphid avoidance was analyzed in in choice assays as described in the Examples.

Within *P. syringae*, the dominant fluorescent molecule is pyoverdine, which is a siderophore used for acquiring iron from the environment, that also produces blue or blue-green fluorescence [10]. To determine if pyoverdine could be responsible for the observed avoidance, we performed choice assays using a pyoverdine-deficient mutant of Psy B278a on plants. Compared to the wild type strain, aphids showed no avoidance of the mutant, which did not produce visible fluorescence (FIG. 3A-C; wild type vs. mutant GLMM: $\chi^2_1$=45.37, p<0.001; probability of avoiding mutant: p=0.51, 95% CI=0.48–0.54). Pyoverdine production appears to be necessary to cause visual avoidance of bacteria by pea aphids.

Because avoidance and virulence were correlated among *P. syringae* strains, we tested whether pyoverdine production could be directly responsible for virulence to pea aphids. We performed virulence assays using oral infection in artificial diet by the pyoverdine-deficient mutant. Pea aphids infected with the pyoverdine-deficient mutant showed statistically indistinguishable death rates compared to those infected with the wild type Psy B278a strain, demonstrating that pyoverdine is not responsible for aphid death in this strain (FIG. 3D; log rank test of Kaplan-Meier survival curves: $\chi^2_1$=0.50, p=0.46). Genes required for pyoverdine production have been identified in most *P. syringae* genomes, however expression levels have been found to vary by strain and environmental context [21, 22]. In some strains, expression has been linked to epiphytic growth ability and therefore aphids may commonly encounter pyoverdine producing strains on plants [23]. Levels of pyoverdine production, or the specific molecule produced, may not be sufficient in all strains to cause avoidance, and in such cases application of the bacteria as described herein can be supplemented if desired with additional pyoverdine. Pyoverdine production may correlate with virulence to aphids as they are both linked to epiphytic growth ability, and may be a useful visual cue [9].

Example 4

Pyoverdine Mediated Avoidance is Consistent Across Light Conditions

We posited that for aphids to use pyoverdine as an indication of pathogens, aphids should be able to detect pyoverdine across lighting conditions, including varied levels of overall brightness and amounts of UV light, as they might encounter naturally. To test this, we performed choice assays using wild type Psy B728a and the pyoverdine-deficient mutant of this strain under both UV blocking and UV transmitting plastic and varied lighting conditions. We found that brightness did affect avoidance, as aphids avoided wild type Psy B728a under medium, high, and shaded (high but indirect light) light conditions, but not low light conditions. Increasing brightness increased the mean avoidance even under shaded conditions with no direct light, suggesting that although the amount of available light may impact avoidance, light does not need to directly illuminate leaves for aphids to detect virulent bacteria (FIG. 6). These effects were dependent upon the amount of UV light available, rather than overall light intensity, and the presence of the fluorescent molecule pyoverdine, as avoidance only occurred under UV transmitting plastic when the wild type strain was present, and not in any other treatment (FIG. 6; UV-transmitting vs. UV-blocking plexiglass GLMM: $\chi^2_1$=24.68, p<0.001). Moreover, the addition of UV light to the medium lighting condition increased the mean avoidance to similar values seen under high light, but again only under UV transmitting plastic. These results support the position that both UV light and pyoverdine production are required for avoidance of virulent *P. syringae* and further suggest that the amount of UV light present can influence levels of avoidance. Although levels of light can influence avoidance, avoidance occurred under varying levels of UV (FIG. 7), even when light was only indirect (shaded), indicating that this phenomenon may be common under varied environmental lighting conditions.

Example 5

Pyoverdine Fluorescence as a Potential Visual Cue

To determine if pyoverdine fluorescence could be a visual cue used by aphids we compared the wavelengths of pyoverdine fluorescence to the visual sensitivities of aphids and to the spectra of leaves coated with epiphytic bacteria either producing or not producing pyoverdine. First, we generated a fluorescence excitation-emission matrix for a suspension of the wild type pyoverdine-producing strain Psy B728a using a spectrofluorometer (FIG. 4A). Second, we contrasted this with a matrix of the pyoverdine-deficient knockout strain (FIG. 4B). Wild type Psy B728a bacteria has the capacity to re-emit many short wavelengths of light as longer wavelengths (i.e. fluorescence), but differs most strongly in emission spectra from the pyoverdine knockout when excited by light of wavelengths 350 nm and 400 nm, which is consistent with previously the determined peak excitation values of pyoverdine from a related bacterial species, Pseudomonasfluorescens [24]. We observed a strong concordance between the cumulative, normalized fluorescence emission curve of wild type Psy B728a and the visual sensitivities of aphids (FIG. 4C). The apparent match between aphid visual sensitivities and the cumulative fluorescence emission spectra of the wild type Psy B728a strain supports the results of the behavioral assays suggesting that aphids are particularly well suited to detecting pyoverdine fluorescence.

In addition to examining the fluorescent profile of bacterial suspensions, we also used a UV-VIS reflectance spectrometer to estimate relative excitance from fava bean leaves coated with epiphytic populations of bacteria that differed in both aphid avoidance and virulence to aphids. Excitance values, which capture both reflectance and fluorescence, from leaves with epiphytic bacterial populations were evaluated using an aphid visual model incorporating the known spectral sensitivities of a closely related aphid species, *Myzus persicae* (FIG. 4C) [25]. This model revealed significant differences between control leaves and leaves colonized with behaviorally-avoided bacterial strains, as well as between leaves coated with differentially avoided bacteria (Table 1, FIG. 8). Avoided bacterial strains on leaves showed excitance curves that were blue-shifted (see hue statistics; Table 1) in a range of wavelengths overlapping with the pyoverdine fluorescence emission (gray regions of FIG. 4C, 4D), supporting the notion that pyoverdine fluorescence facilitates avoidance (FIG. 4D, FIG. 8). Additionally, it appears that there may be a threshold color-shift required for avoidance, as leaves coated with unavoided bacterial strains tended to be more blue-photoreceptor-stimulating than leaves painted with a control solution, but less-blue-photoreceptor-stimulating than leaves painted with avoided strains (FIG. 8, Table 1). Together with the present findings that both UV light and the known fluorescence compound pyoverdine are required for aphid avoidance of virulent *P. syringae* strains, these results reinforce aspects of this disclosure that in part demonstrate pyoverdine fluorescence mediates aphid avoidance.

Example 6

Cell Lysate Experiments:

In order to determine if aphids avoid crude pyoverdine extracts in the absence of living bacteria, two experiments were performed: 1) treatments of leaves with spent media (in which bacteria have been removed after growing and excreting pyoverdine overnight), and 2) treatments with crude cell lysates of bacterial cultures. Both treatments led to higher avoidance than bacterial cells on their own (~90% of aphids on control leaves in excised leaf pairs, compared to ~70% of aphids avoiding leaves with living bacteria). Without intending to be constrained by any particular theory, it is considered that this is likely due to greater amounts of pyoverdine produced by a dense cell culture grown under iron limited conditions than by a natural bacterial population on a leaf. These results indicate that pyoverdine in the absence of intact bacteria can be used as an effective deterrent.

Example 7

Cell Density Experiments:

Different densities of avoided bacterial cells on fava bean leaves were tested to determine how many cells are needed for avoidance. Aphids avoided leaves with $10^6$ CFU/3 $mm^2$ disc cells per leaf disc. Average densities of naturally occurring *P. syringae* populations on bean plants are typically much lower than this, more commonly around $10^5$ cells per leaf. Therefore, natural populations of *P. syringae* are likely not sufficient to deter aphids. In contrast, when cells are sprayed on leaves according to embodiments of this disclosure, populations densities can reach ~$10^8$ cells per leaf disc, which is sufficient for high avoidance.

Example 8

The following materials and methods were used to produce results described herein.

Insects

Lab colonies of *A. pisum* were reared at 21° C. and a light:dark 16:8 hour cycle. Under long day summer-like conditions pea aphids will reproduce parthenogenetically as clones. Colonies were housed in breeding tents containing several fava bean (*Vicia faba*) plants that were rotated out for fresh plants several times a week to maintain healthy conditions. We used aphid clone CWR09/18, which does not harbor any endosymbionts other than *Buchnera aphidicola* [27].

Bacteria

Bacterial cultures were grown on King's B (KB) media with rifampicin (50 ng/μL). Culture plates were incubated at 27° C. and overnight cultures were grown in an incubator shaker set at 27° C. and 300 rpm. Strain designations and origins are listed in Table 2.

Choice Assays

Choice assays were performed on either whole plants, excised leaf pairs, or with artificial aphid diet. For assays using whole plants, two week old fava bean plants were used. The apical leaf pair of each plant was removed to encourage aphids to choose among fully expanded leaves. Each plant had three leaf pairs distributed in different orientations around the stem of the plant. Within each leaf pair one leaflet was painted with a 10 mM $MgCl_2$ control solution and the other was painted with bacteria suspended in 10 mM $MgCl_2$ solution. Solution was applied to the leaf surface with a sterile cotton swab until the surface was visibly saturated but not dripping. Bacterial suspensions were made from overnight cultures, which were pelleted, washed and resuspended using 10 mM $MgCl_2$ then adjusted to an optical density of 1.0 ($OD_{600}$) using a WPA CO 8000 Cell Density Meter which measures optical density at 600 nm. Leaves were allowed to dry and then approximately 80 mixed age aphid nymphs (not yet reproductive) were introduced on the soil the base of the plant. Plants were caged individually and incubated at 21° C. and 80% relative humidity under a light:dark 16:8 hour cycle with full spectrum cool blue fluorescent grow lights (54 W T5 fluorescent with 6400K color temperature approximating daylight) positions above the plants. Pea aphids feed on the undersides of leaves and on stems and we never observed aphids feeding on the upper surfaces of leaves in these experiments. Because fava bean stems would be difficult to paint with bacteria in a controlled manner we focused on aphids feeding on leaves. Our experimental set up mimicked natural conditions in which aphids would be viewing the undersides of leaves, in that they would be encountering the undersides of leaves that are illuminated from above. Placing aphids at the base of the plant forced them to approach each leaf pair via the stem and petiole, so they must choose one leaflet or the other (control or bacteria) from the petiole. The number of aphids feeding on control and bacterial leaves was observed after four hours and then every 7-17 hours for three days for a total of 4 time points. Aphids feeding on stems did not participate in the experiment and were not included in analyses. Eight plants were used in each replicate and assays were replicated three times for each strain. By four hours most aphids had settled to feed and we found that plants had 30-70 aphids feeding on leaves. Additional time points were recorded as well, but we found that numbers of aphids on control versus bacterial leaves stayed consistent across the time frame of the experiment, so except when analyzing change over time (FIG. 5), we used data from four hours for analyses. At least 444 aphids were included in analyses for each strain.

Under dark conditions aphids were greatly delayed in settling to feed on whole plants. Therefore, to test aphid preference under dark and no UV light conditions choice assays were done using excised leaves. Methods for assays on excised leaves followed whole plant assays, except that a single leaf pair was removed from a plant and the petiole was embedded in a wedge of water agar in a petri dish. Mixed age aphid nymphs were introduced into petri dishes (not onto the leaf directly) and allowed to crawl onto the underside of the leaf. For assays testing preference in the absence of vision, two growth chambers with the same temperature and humidity were used, with lights turned off in one chamber and the other was illuminated with vertical fluorescent lights fixed in the door. For assays testing the importance of UV light on preference, plates were incubated in the same growth chamber but half of the plates were kept under a box constructed out of UV-filtering plexiglass (OP-3/UF-5), which filters out 98% of UV light. Each assay had five plates in each treatment and each treatment was replicated two (dark) or three (UV) times. Approximately 15-25 aphids per dish settled to feed on leaves during experiments in the dark and approximately 30-50 per dish settled during experiments under UV-filtering, for a total of at least n=196 per dark/light treatment and n=664 per UV/UV filtered treatment. The highly virulent and highly avoided strain Psy B728a was used for these experiments.

In order to determine if aphids would still avoid virulent strains in the absence of a plant, we performed assays testing for aphid preference between strain Psy B728a suspended in artificial aphid diet or artificial aphid diet alone. Bacterial suspensions were prepared as described above and corrected to an $OD_{600}$ of 0.8. This suspension was mixed in a 1:5 ratio with artificial diet [28]. Control diet was made with a similar ratio of 10 mM $MgCl_2$. 96-well plates were divided into 4 quadrants with empty rows in between quadrants. Wells in diagonally positioned quadrants were filled with the same treatment, either bacterial suspension or control, with two quadrants for each treatment. Parafilm was stretched across the plate to make a feeding sachet and this was inverted over a plastic box containing approximately 200 mixed age pea aphid nymphs and secured with parafilm so that the aphids could access all of the feeding sachet wells. The number of aphids feeding in each quadrant was recorded every half hour for four hours and then once 20-22 hours later. This assay was replicated three times.

Light Controlled Assays

To determine the influence of varied lighting conditions on aphid avoidance of virulent *P. syringae*, we performed choice assays with varied light brightness with and without UV light. These experiments were done with excised leaves in petri dishes as described above and leaves were treated with either wild type Psy B728a or the pyoverdine deficient mutant of this strain. One leaflet in each leaf pair was painted with bacterial suspensions as detailed above or a control solution of 10 mM $MgCl_2$. For each experiment, 7 plates of each bacterial treatment were placed under UV-filtering plexiglass as above, or under UV-transmitting plexiglass (UVT acrylic, EMCO plastics), which allows for transmission of wavelengths in the UV spectrum. Dishes were elevated approximately four inches above a diffusely reflecting, spectrally flat polytetrafluoroethylene surface to allow light exposure on the underside of leaves and fluorescent bulbs were suspended approximately three feet above them. Experiments were conducted in high-brightness (8 fluorescent bulbs), medium-brightness (4 bulbs) and low-brightness (2 bulbs) light environments. An additional assay was done using medium-brightness with supplemental UV light from two 60 W fluorescent blacklight bulbs (Adkins Professional lighting) to test for the effect of supplemental UV light. Lastly, in an experiment with high-brightness (8 bulbs) we covered the tops of petri dishes with aluminum foil so that the leaves were shaded—enabling us to determine the possible importance of light transmitting through leaves in influencing aphid avoidance. These experiments were performed at 21° C. and ambient humidity under a light:dark 16:8 hour cycle and replicated twice for each lighting condition. Aphids feeding on leaves were observed at four hours after set up and the minimal sample size was 771 aphids per treatment.

Infection Assay

To test if avoidance leads to a decreased rate of *P. syringae* infection in pea aphids we determined infection rates in aphids that either had a choice between bacterial leaves and control leaves or only had access to bacterial leaves. Aphids given a choice were placed on plants treated as above for on plant assays, with one leaflet per leaf pair painted with Psy B728a and the other with 10 mM $MgCl_2$ and the top of the plant removed to discourage settling there. Aphids with no choice were placed on plants with all leaves painted with bacteria. However, more of the top of the plant had been removed so that the total number of leaflets with bacteria, and therefore total bacterial leaf surface area, was similar to choice plants. Aphids were left on plants for 48 hours and then 30 aphids were collected from each plant, spread equally across control and bacterial leaves. Each treatment included two plants and this experiment was replicated twice with a total of 240 aphids sampled. Aphids were individually surface sterilized by washing with 70% ethanol, washed in 10 mM $MgCl_2$, and then homogenized in 100 μL of 10 mM $MgCl_2$. The entire homogenate of each whole aphid was plated onto a KB with rifampicin (50 ng/μL) plate and incubated for 48 hours. Colonies were counted and an aphid was considered positive for infection if greater than five colonies were present.

Virulence Assay

In vitro oral pathogenicity assays followed the known methods in [9] and utilized the wild type Psy B728a strain as well as a pyoverdine-deficient mutant with a deletion of the gene pvdL. Briefly, bacterial suspensions were mixed with artificial aphid diet as described above and 200 μl of the suspension or control diet was placed into each well of a 96-well plate to make a feeding sachet. Individual age-controlled (5 days old, approximately third instar) aphids were placed in wells of a second plate and arranged below the feeding sachet. Aphids were allowed to feed on diet with bacterial suspensions for 24 hours under UV-filtering plastic to keep feeding and infection rates consistent across treatments. After 24 hours the feeding sachet was replaced with another sachet of sterile diet only. The diet was refreshed again after another 24 and 48 hours. Twice daily, at diet changes and time points between them, aphid death was recorded. An aphid was assumed dead if it had turned brown or was at the bottom of the well (not feeding) and did not move when agitated.

Statistical Analysis

All statistical analyses were conducted in R version 3.3.1 [29]. For datasets investigating choice assays, response variables were binary counts (choice of a control leaf vs. choice of a bacteria-coated leaf; infected or not infected) and so generalized linear mixed-effects models (GLMM) using binomial error distributions were employed from the R package lme4 [30]. Experimental blocks were included within the GLMMs as random factors. Explanatory variables (in separate models: 1. dark vs. natural light, 2. UV block vs. natural light, and 3. mutant vs. wildtype B728a) were added to null models and their significance tested using likelihood ratio tests of the two models to determine whether or not they had a significant effect on aphids' choices.

To determine whether aphids on plants avoided leaves coated with *P. syringae*, to the extent that significantly more than 50% of the aphids chose the control leaves on the plant, we conducted a GLMM as before, but removed the intercept of the model by including −1 as a variable. This gave us a p-value testing the null hypothesis that the probability of avoiding the bacteria was 0.5. To obtain probabilities with confidence intervals from the models, we used the package 'lsmeans' [31].

In order to demonstrate that pyoverdine is not responsible for aphid death, we conducted survival analysis using log rank tests of pairwise comparisons of Kaplan-Meier survival curves, using the R packages 'survival' [32] and 'survminer' [33]. We also conducted a Pearson's product-moment correlation between the virulence of strains and the level of avoidance by aphids (four hours after introducing them to a plant), with an alternative hypothesis of a positive relationship between the two.

Reflectance, Irradiance, Fluorescence Analysis

For each of the strains in Table 2 one leaf pair was painted with a bacterial suspension prepared as described above. Leaves were allowed to dry and the undersides were used for reflectance measurements. We used a UV-VIS spectrometer (FLAME-S—UV-VIS, Ocean Optics, Dunedin, Florida, USA), a pulsed xenon light source (PX2, Ocean Optics), and bifurcated fiber optic measuring probe (which allowed light from the xenon bulb to be directed onto the surface of the leaf and transferring reflected light from the leaf back to the spectrometer) to measure the influence of epiphytic bacterial populations on the wavelengths of light emitted from infected leaves. The spectrometer probe was held at 90' and at a distance of 10 mm from the surface of the leaf and measurements were calibrated against a 99% white diffuse reflectance standard (WS-1-SL, Ocean Optics, USA). We averaged 10 scans for each measurement (integration time=60 ms, boxcar width=20 nm), and took 20 measurements per leaf. We used the software OceanView (Ocean Optics) to record reflectance spectra. Additionally, we measured the light environment of our experimental conditions using a Qstick miniature spectrometer (RGB photonics, Kerlheim, Germany). Five irradiance measurements were collected and averaged per lighting condition to obtain representative irradiance measurements.

Fluorescence excitation/emission matrices were obtained using samples measured in PTI Felix 32 Spectrofluorometer (Photon Technology International) with a LPS-220 lamp power supply in conjunction with FeliX32™ Advanced Fluorescence Analysis Software Package. We measured suspensions of wild type Psy B728a bacteria and pvdI (pyoverdine-deficient) mutant bacteria suspended in King's B media, as well as a sample containing only media (which we subsequently subtracted from our fluorescence measures of the bacteria). We collected emission data at 1 nm intervals from single excitation wavelengths spanning 340-425 nm, spaced at 5 nm intervals (and interpolated our matrix to 1 nm resolution in the excitation wavelength axis).

Visual Modeling

We employed a visual modeling approach to estimate how leaves coated with different strains of epiphytic bacteria might appear to aphids. Specifically, we implemented a noise-receptor model estimate [34] of chromatic contrasts using package Pavo in R [35] by first calculating receptor-specific quantum catch values where $Q_i$, denotes one of the three classes of aphid photoreceptors (UV=ultraviolet, B=blue, G=green; FIG. 8) as:

$$Q_i = \int_{300}^{700} I(\lambda) S_i(\lambda) R(\lambda) d\lambda$$

where $I(\lambda)$ is the illumination spectrum, $S_i(\lambda)$ is the spectral sensitivity function of receptor i (FIG. 8), and $R(\lambda)$ is the reflectance spectrum of the leaf. In this case, rather than the reflectance spectra, we used normalized excitance curves to estimate the combined influence of reflectance and fluorescence on the appearance of bacterial-coated leaves. Additionally, we used ideal illumination spectra (i.e. irradiance=1 at all wavelengths) for our primary analyses. After obtaining quantum catch values for each photoreceptor for each color, we then calculated chromatic contrasts between every pairwise combination of measurements in units of Just Noticeable Differences (JNDs) using the equation:

$$\Delta S = \sqrt{\frac{e_{UV}^2(\Delta f_G - \Delta f_B)^2 + e_B^2(\Delta f_G - \Delta f_{UV})^2 + e_G^2(\Delta f_{UV} - \Delta f_B)^2}{(e_{UV}e_B)^2 + (e_{UV}e_G)^2 + (e_B e_G)^2}}$$

where $\Delta f_i$ is the difference in log of quantum catches for receptor i between color pairs and $e_i$ is the internal receptor noise for each receptor class (modelled uniformly as 0.1), implemented via the coldist function in Pavo. Using the chromatic contrasts among all color measurements, we next calculated the Cartesian coordinates for each color measurement in "aphid color space" using known scripts [36], wherein perceptual distances between colors are preserved regardless of directionality and correspond to the Euclidean distance between points. Within this color space, distance from the achromatic origin (white, gray, black) provides a measure of chroma, and the angle ($\theta$) between the vector connecting the achromatic origin and pure UV cone stimulation and the vector connecting the achromatic origin and the Cartesian coordinates of a given color provides a measure of hue (sensu[37]; FIG. 8).

Following quantification of visual parameters, we compared the appearance of the different strains using linear mixed models with leaves as random variables with the package lme4 [30] in R [29]. Additionally, we conducted post-hoc Tukey tests with the glht function in the multcomp package [38].

Figure 4:
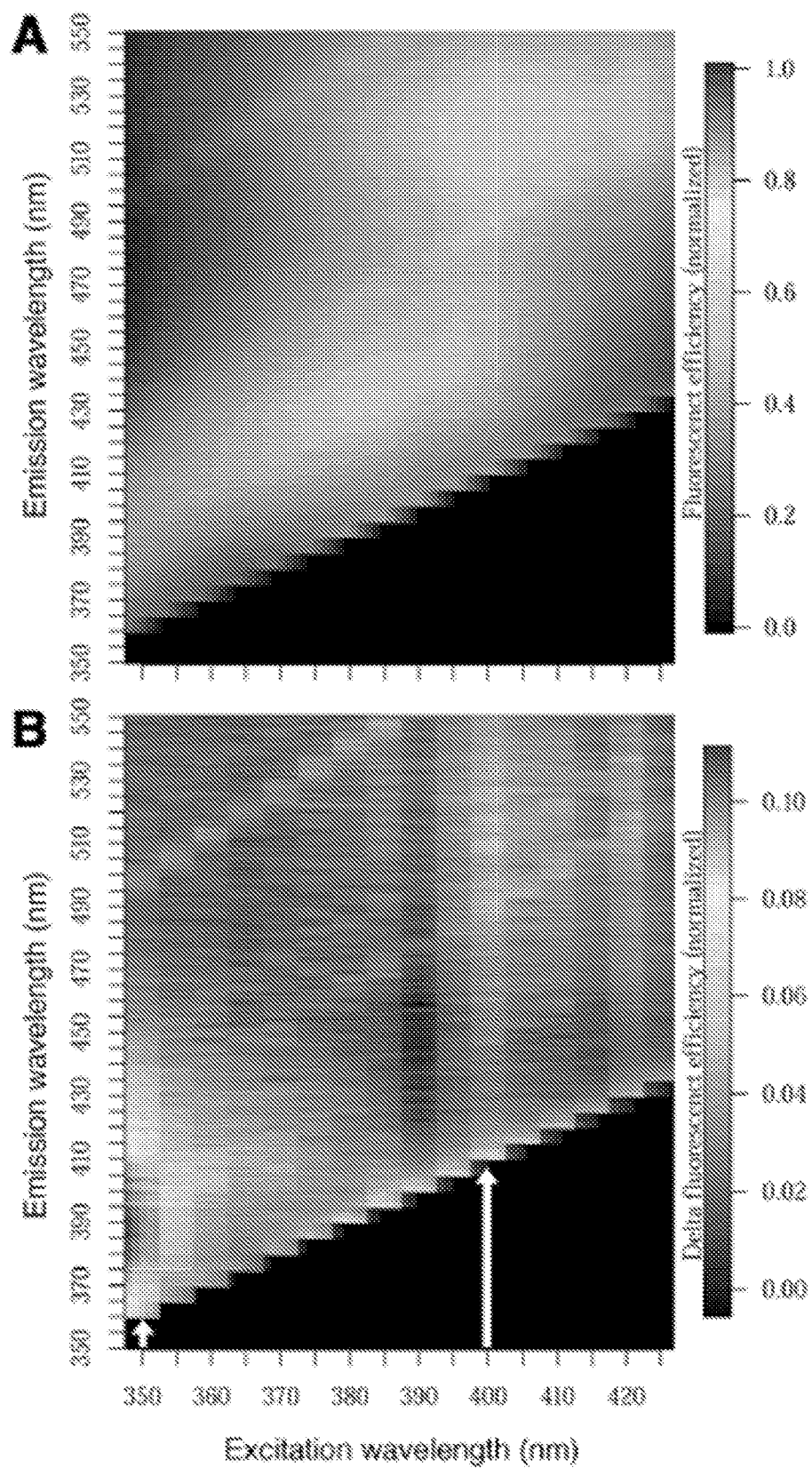
FIG. 4. Pyoverdine Fluorescence Compared to Aphid Visual Sensitivities and Excitance for Leaves with Varied Epiphytic Bacterial Strains. (A) Excitation/emission matrix illustrating normalized fluorescence efficiency of wild type Psy B728a bacteria. (B) Differential fluorescence efficiency matrix illustrating the excitation wavelengths most responsible (white arrows) for differences between wild type and pyoverdine-deficient mutant bacteria. (C) Normalized sensitivity curves for the green peach aphid Myzus persicae [25, 26] with cumulative fluorescence emission from wild type Psy B728a bacteria overlaid, illustrating high concordance between light sensitivity of the aphids and the fluorescence emission of the bacteria. (D) Idealized excitance (reflectance+fluorescence) spectra for fava bean leaves coated with different bacterial strains. Lines represent mean values from 40 measurements collected from 4 leaves per treatment (10 measurements/leaf), and colored shaded regions represent the standard deviations. The vertical grey bar indicates the region of wavelengths over which fluorescence of Psy B728a occurs. The wavelengths showing the most variation in excitance between leaves with different treatments correspond to the wavelengths of highest Psy B728a fluorescence, with avoided strains producing higher excitance.
Figure 4:
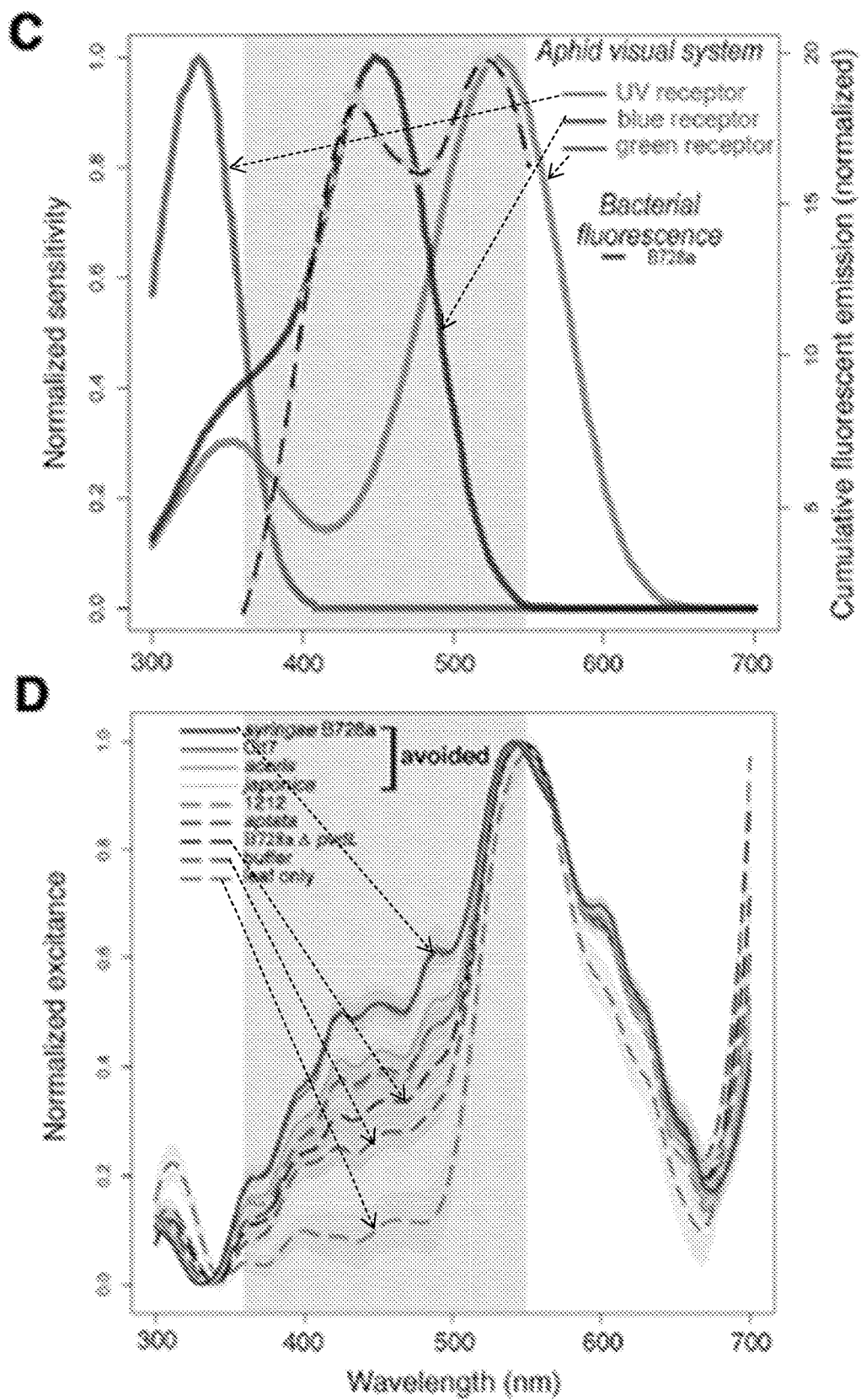

It will be recognized from the foregoing that a suite of behavioral assays using genetically diverse bacterial strains, along with visual modeling and fluorescence measurements, reveal how virulent P. syringae strains may be visually distinguishable to aphids, supporting embodiments of the present disclosure that exploits the ability of aphids to use vision to preferentially avoid feeding on plants colonized with virulent epiphytic bacteria. This demonstrates that UV-based fluorescence mediated by the bacterial product pyoverdine may be a reliable indicator of the presence of highly virulent bacteria, and that detection and avoidance of fluorescence may benefit aphids by reducing infection risks. This avoidance mechanism has 1 applications in biological control of aphid pest species, as described above.

TABLE 1

Summary Statistics from Linear Mixed Models Comparing Receptor Noise-Limited-Derived Chroma and Hue Measurements Across Epiphytic Treatments, Related to FIG. 4.

| | Estimate | Std. Error | t value | p-value relative to buffer leaves | Post-hoc category | Behavioral avoidance |
|---|---|---|---|---|---|---|
| | | | Chroma | | | |
| (Intercept) | 14.90 | 0.27 | 55.26 | | — | |
| B728a Δ pvdl | 0.86 | 0.38 | 2.25 | 0.49 | AB | no |
| *aptata* | 1.28 | 0.38 | 3.35 | 0.02 | B | no |
| 1212 | 0.94 | 0.38 | 2.48 | 0.29 | AB | no |

TABLE 1-continued Summary Statistics from Linear Mixed Models Comparing
Receptor Noise-Limited-Derived Chroma and Hue Measurements
Across Epiphytic Treatments, Related to FIG. 4.

|  | Estimate | Std. Error | t value | p-value relative to buffer leaves | Post-hoc category | Behavioral avoidance |
|---|---|---|---|---|---|---|
| aceris | 1.69 | 0.38 | 4.44 | <0.001 | B | yes |
| japonica | 1.83 | 0.38 | 4.80 | <0.0001 | B | yes |
| Cit7 | 1.29 | 0.38 | 3.38 | 0.02 | B | yes |
| syringae B728a | 1.70 | 0.38 | 4.45 | <0.001 | B | yes |
| Hue |  |  |  |  |  |  |
| (Intercept) | 249.04 | 0.78 | 318.76 | — |  |  |
| B728a Δ pvdl | −4.89 | 1.10 | −4.42 | <0.001 | W | no |
| aptata | −8.28 | 1.10 | −7.49 | <0.0001 | X | no |
| 1212 | −7.86 | 1.10 | −7.11 | <0.0001 | WX | no |
| aceris | −10.27 | 1.10 | −9.30 | <0.0001 | XY | yes |
| japonica | −13.73 | 1.10 | −12.43 | <0.0001 | Z | yes |
| Cit7 | −12.81 | 1.10 | −11.59 | <0.0001 | YZ | yes |
| syringae B728a | −13.24 | 1.10 | −11.99 | <0.0001 | YZ | yes |

In Table 1, chroma and hue values obtained from a model of aphid vision indicate that leaves infected with different strains of epiphetic bacteria likely appear different to aphids (FIG. 8). Specifically, leaves with virulent, avoided strains are distinct from control leaves (painted only with buffer) and those infected with the pyoverdine-deficient mutant. Comparisons with control (buffer only) leaves indicates that aphids should be able to detect all bacterially-coated leaves; that they do not avoid several of the strains suggest that specific visual signature is required for avoidance (not merely detectable differences).\

TABLE 2

Summary of P. syringae Strains Used Here, Related to FIG. 1.

| Species | Pathovar | Strain | Group[a] | Source[b] | Reference[c] |
|---|---|---|---|---|---|
| Pseudomonas syringae | tomato | DC3000 | 1 | Solanum lycopersicum | [39] |
| Pseudomonas syringae | syringae | B728a | 2 | Phaseolus vulgaris | [40] |
| Pseudomonas syringae | syringae | 1212 | 2 | Pisum sativum | [41] |
| Pseudomonas syringae | japonica | MAFF 301072 PT | 2 | Hordeum vulgare | [42] |
| Pseudomonas syringae | aptata | DSM50252 | 2 | Beta vulgaris | [43] |
| Pseudomonas syringae | aceris | MAFF 302273 PT | 2 | Acer sp. | [44] |
| Pseudomonas syringae | N/A | Cit7 | 2 | citrus leaf surface | [45] |
| Pseudomonas savastanoi | phaseolicola | 1448a | 3 | Phaseolus vulgaris | [46] |

[a] phylogroup designation [47]
[b] plant isolation source
[c] origin reference

The following list of references is not an indication that any particular reference is material to patentability.

REFERENCES

1. Blackman, R. L. and Eastop, V. F. (2016). Wiley: Aphids on the World's Crops: An identification and information guide, 2nd edition.
2. Ng, J. C. K., and Perry, K. L. (2004). Transmission of plant viruses by aphid vectors. Mol. Plant Pathol. 5, 505-511.
3. Nadarasah, G., and Stavrinides, J. (2011). Insects as alternative hosts for phytopathogenic bacteria. FEMS Microbiol. Rev. 35, 555-575.
4. Grenier, A.-M., Duport, G., Pages, S., Condemine, G., and Rahbe, Y. (2006). The phytopathogen Dickeya dadantii (Envinia chrysanthemi 3937) is a pathogen of the pea aphid. Appl. Environ. Microbiol. 72, 1956-1965.
5. Harada, H., and Ishikawa, H. (1997). Experimental pathogenicity of Envinia aphidicola to pea aphid, Acyrthosiphon pisum. J. Gen. Appl. Microbiol. 43, 363-367.
6. Gerardo, N. M., Altincicek, B., Anselme, C., Atamian, H., Barribeau, S. M., Vos, M. de, Duncan, E. J., Evans, J. D., Gabaldón, T., Ghanim, M., et al. (2010). Immunity and other defenses in pea aphids, Acyrthosiphon pisum. Genome Biol. 11, R21.
7. Laughton, A. M., Garcia, J. R., Altincicek, B., Strand, M. R., and Gerardo, N. M. (2011). Characterisation of immune responses in the pea aphid, Acyrthosiphon pisum. J. Insect Physiol. 57, 830-839.
8. Hirano, S. S., and Upper, C. D. (2000). Bacteria in the leaf ecosystem with emphasis on Pseudomonas syringae—a pathogen, ice nucleus, and epiphyte. Microbiol. Mol. Biol. Rev. 64, 624-653.
9. Smee, M. R., Baltrus, D. A., and Hendry, T. A. (2017). Entomopathogenicity to two hemipteran insects is common but variable across epiphytic Pseudomonas syringae strains. Front. Plant Sci. 8, 2149.
10. Visca, P., Imperi, F., and Lamont, I. L. (2007). Pyoverdine siderophores: from biogenesis to biosignificance. Trends Microbiol. 15, 22-30.
11. Stavrinides, J., McCloskey, J. K., and Ochman, H. (2009). Pea aphid as both host and vector for the phytopathogenic bacterium Pseudomonas syringae. Appl. Environ. Microbiol. 75, 2230-2235.
12. Costechareyre, D., Balmand, S., Condemine, G., and Rahbe, Y. (2012). Dickeya dadantii, a Plant Pathogenic Bacterium Producing Cyt-Like Entomotoxins, Causes Septicemia in the Pea Aphid Acyrthosiphon pisum. PLoS ONE 7, e30702.
13. Hendry, T. A., Clark, K. J., and Baltrus, D. A. (2016). A highly infective plant-associated bacterium influences reproductive rates in pea aphids. Open Sci. 3, 150478.
14. Lukasik, P., Guo, H., Asch, M., Ferrari, J., and Godfray, H. C. J. (2013). Protection against a fungal pathogen conferred by the aphid facultative endosymbionts *Rickettsia* and *Spiroplasma* is expressed in multiple host genotypes and species and is not influenced by co-infection with another symbiont. J. Evol. Biol. 26, 2654-2661.
15. Hendry, T. A., Hunter, M. S., and Baltrus, D. A. (2014). The facultative symbiont *Rickettsia* protects an invasive whitefly against entomopathogenic *Pseudomonas syringae* strains. Appl. Environ. Microbiol. 80, 7161-7168.
16. Parker, B. J., Barribeau, S. M., Laughton, A. M., de Roode, J. C., and Gerardo, N. M. (2011). Non-immunological defense in an evolutionary framework. Trends Ecol. Evol. 26, 242-248.
17. Lindow, S. E. (1987). Competitive exclusion of epiphytic bacteria by ice—*Pseudomonas syringae* mutants. Appl. Environ. Microbiol. 53, 2520-2527.
18. Feil, H., Feil, W. S., Chain, P., Larimer, F., DiBartolo, G., Copeland, A., Lykidis, A., Trong, S., Nolan, M., Goltsman, E., et al. (2005). Comparison of the complete genome sequences of *Pseudomonas syringae* pv. syringae B728a and pv. tomato DC3000. Proc. Natl. Acad. Sci. U.S.A 102, 11064-11069.
19. Doring, T. F. (2014). How aphids find their host plants, and how they don't. Ann. Appl. Biol. 165, 3-26.
20. Doring, T. F., and Chittka, L. (2007). Visual ecology of aphids—a critical review on the role of colours in host finding. Arthropod-Plant Interact. 1, 3-16.
21. Baltrus, D. A., Hendry, T. A., and Hockett, Kevin L. (2014). Ecological genomics of *Pseudomonas syringae*. In Genomics of plant-associated bacteria (Berlin: Springer-Verlag), pp. 59-77.
22. Joyner, D. C., and Lindow, S. E. (2000). Heterogeneity of iron bioavailability on plants assessed with a whole-cell GFP-based bacterial biosensor. Microbiol. Read. Engl. 146 (Pt 10), 2435-2445.
23. Wensing, A., Braun, S. D., Buttner, P., Expert, D., Volksch, B., Ullrich, M. S., and Weingart, H. (2010). Impact of siderophore production by *Pseudomonas syringae* pv. syringae 22d/93 on epiphytic fitness and biocontrol activity against *Pseudomonas syringae* pv. glycinea 1a/96. Appl. Environ. Microbiol. 76, 2704-2711.
24. Meyer, J. M., and Abdallah, M. A. (1978). The fluorescent pigment of *Pseudomonas fluorescens*: biosynthesis, purification and physicochemical properties. Microbiology 107, 319-328.
25. Kirchner, S. M., Doring, T. F., and Saucke, H. (2005). Evidence for trichromacy in the green peach aphid, *Myzus persicae* (Sulz.) (Hemiptera: Aphididae). J. Insect Physiol. 51, 1255-1260.
26. Stavenga, D. G., Smits, R. P., and Hoenders, B. J. (1993). Simple exponential functions describing the absorbance bands of visual pigment spectra. Vision Res. 33, 1011-1017.
27. Macdonald, S. J., Lin, G. G., Russell, C. W., Thomas, G. H., and Douglas, A. E. (2012). The central role of the host cell in symbiotic nitrogen metabolism. Proc. R. Soc. B Biol. Sci. 279, 2965-2973.
28. Prosser, W. A., and Douglas, A. E. (1992). A test of the hypotheses that nitrogen is upgraded and recycled in an aphid (*Acyrthosiphon pisum*) symbiosis. J. Insect Physiol. 38, 93-99.
29. R Core Team (2016). R: A language and environment for statistical computing. R Foundation for Statistical Computing, Vienna, Austria. URL http://www.R-project.org/ 30.
30. Bates, D., Machler, M., Bolker, B. M., and Walker, S. C. (2015). Fitting linear mixed-effects models using lme4. J. Stat. Softw. 67, 1-48.
31. Lenth, R. V. (2016). Least-squares means: The R package lsmeans. J. Stat. Softw. 69, 1-33.
32. Therneau, T. M. (2017). A package for survival analysis in S.
33. Kassambara, A., and Kosinski, M. (2017). *Survminer: drawing survival curves using "ggplot2". R package version 0.4.0.*
34. Vorobyev, M., and Osorio, D. (1998). Receptor noise as a determinant of colour thresholds. Proc. Biol. Sci. 265, 351-358.
35. Maia, R., Eliason, C. M., Bitton, P.-P., Doucet, S. M., and Shawkey, M. D. (2013). pavo: an R package for the analysis, visualization and organization of spectral data. Methods Ecol. Evol. 4, 906-913.
36. Pike, T. W. (2012). Preserving perceptual distances in chromaticity diagrams. Behav. Ecol. 23, 723-728.
37. Endler, J. A., and Mielke, P. W. (2005). Comparing entire colour patterns as birds see them. Biol. J. Linn. Soc. 86, 405-431.
38. Hothorn, T., Bretz, F., and Westfall, P. (2008). Simultaneous inference in general parametric models. Biom. J. Biom. Z. 50, 346-363.
39. Cuppels, D. A. (1986). Generation and characterization of Tn5 insertion mutations in *Pseudomonas syringae* pv. tomato. Appl. Environ. Microbiol. 51, 323-327.
40. Loper, J. E. (1987). Lack of evidence for in situ fluorescent pigment production by *Pseudomonas syringae* pv. syringae on bean leaf surfaces. Phytopathology 77, 1449.
41. Gilmartin, C. R. (1997). "The detection and characterization of avirulence genes in *Pseudomonas syringae* pathovars," thesis. University of the West of England: Bristol, U.K.
42. Mukoo, H. (1955). On the bacterial black node of barley and wheat and its causal bacteria. Jubil. Publ. Commem. Sixtieth Birthd. Prof Yoshihiko Tochinai Prof Teikichi Fukushi, 153-157.
43. Baltrus, D. A., Nishimura, M. T., Romanchuk, A., Chang, J. H., Mukhtar, M. S., Cherkis, K., Roach, J., Grant, S. R., Jones, C. D., and Dangl, J. L. (2011). Dynamic evolution of pathogenicity revealed by sequencing and comparative genomics of 19 *Pseudomonas syringae* isolates. PLOS Pathog 7, e1002132.
44. Sawada, H., Suzuki, F., Matsuda, I. & Saitou, N. Phylogenetic analysis of *Pseudomonas syringae* pathovars suggests the horizontal gene transfer of argK and the evolutionary stability of hrp gene cluster. J. Mol. Evol. 49, 627-644 (1999)
45. Hirano, S., and Upper, C. (1990). Population biology and epidemiology of *Pseudomonas syringae*. Annu. Rev. Phytopathol. 28, 155-177.
46. Teverson, D. M. (1991). "Genetics of pathogenicity and resistance in the haloblight disease of beans in Africa," thesis. University of Birmingham, Birmingham, U.K.
47. Berge, O., Monteil, C. L., Bartoli, C., Chandeysson, C., Guilbaud, C., Sands, D. C., and Morris, C. E. (2014). A user's guide to a data base of the diversity of *Pseudomonas syringae* and its application to classifying strains in this phylogenetic complex. PLOS ONE 9, e105547.

What is claimed is:

1. A method for reducing on a population of plants an amount of aphids comprising applying to at least some of the plants:

bacteria that are pathogenic to the aphids but have been modified to not produce pyoverdine or to produce less pyoverdine relative to unmodified bacteria.

2. The method of claim 1, further comprising inspecting the plants and determining that the plants are insect free or are in contact with fewer insects than a control.

* * * * *